US007498409B2

(12) United States Patent
Vlach et al.

(10) Patent No.: US 7,498,409 B2
(45) Date of Patent: Mar. 3, 2009

(54) SCREENING ASSAY FOR TLR7, TLR8 AND TLR9 AGONISTS AND ANTAGONISTS

(75) Inventors: Jaromir Vlach, Annandale, NJ (US); Uzma Ayesha Hasan, Lyons (FR); Sandra Dollet, Villeurbanne (FR)

(73) Assignee: Schering Corporation, Kenilworth, NJ (US)

( * ) Notice: Subject to any disclaimer, the term of this patent is extended or adjusted under 35 U.S.C. 154(b) by 136 days.

(21) Appl. No.: 11/387,182

(22) Filed: Mar. 23, 2006

(65) Prior Publication Data

US 2006/0269936 A1 Nov. 30, 2006

Related U.S. Application Data

(60) Provisional application No. 60/665,068, filed on Mar. 24, 2005.

(51) Int. Cl.
*C07K 14/00* (2006.01)
*C40B 30/04* (2006.01)

(52) U.S. Cl. .......................................... 530/350; 506/9

(58) Field of Classification Search ................ 530/350; 506/9

See application file for complete search history.

(56) References Cited

U.S. PATENT DOCUMENTS 6,943,240 B2 * 9/2005 Bauer et al. ................ 536/23.1
7,271,248 B2 * 9/2007 Hardiman et al. ........ 530/387.1
2003/0032090 A1 * 2/2003 Hardiman et al. .......... 435/69.1

FOREIGN PATENT DOCUMENTS

WO WO 98/50547 11/1998
WO WO 01/90151 11/2001

OTHER PUBLICATIONS

Tabeta et al., 2004, Toll-like receptors 9 and 3 as essential components of innate immune defense against mouse cytomegalovirus infection, PNAS, 101(10): 3516-3521.*

Philbin et al., 2005, Identification and characterization of a functional, alternatively spliced Toll-like receptor 7 (TLR7) and genomic disruption of TLR8 in chickens, Immunology, 114: 507-521.*

Gerwirtz et al., Cutting Edge: Bacterial Flagellin Activates Basolaterally Expressed TLR5 to Induce Epithelial Proinflammatory Gene Expression, J. Immunol., 167:1882-1885 (Aug. 2001).

Shirota et al., Novel Roles of CpG Oligodeoxynucleotides as a Leader for the Sampling and Presentation of CpG-Taged Antigen by Dendritic Cells , J. Immunol. 167: 66-74 (Jul. 2001).

Hornung et al., Quantitative Expression of Toll-Like Receptor 1-10 mRNA in Cellular Subsets of Human Peripheral Blood Mononuclear Cells and Sensitivity to CpG Oligodeoxynucleotides, J. Immunol., 168:4, 4351-4537 (May 2002).

Singh et al., Toll-Like Receptors and their Role in Innate Immunity, Current Science, 85:8, 1156-1164 (Oct. 2003).

Michael Rehli, of mice and men: species variations of Toll-like receptor expression, Trends Immunol., 23:8, 375-378 (Aug. 2002).

Bell et al., Leucine-rich repeats and pathogen recognition in Toll-like receptors, Trends Immunol., 24:10, 528-533 (Oct. 2003).

Diebold, et al., Innate Antiviral Responses by Means of TLR7-Mediated Recognition of Single-Stranded RNA, Science, 303:1529-1531 (Mar. 2004).

Heil, et al., Species-Specific Recognition of Single-Stranded RNA via Toll-like Receptor 7 and 8, Science, 303:1526-1528 (Mar. 2004).

Zarember, et al., Tissue Expression of Human Toll-Like Receptors and Differential Regulation of Toll-Like Receptor mRNAs in Leukocytes in Response to Microbes, Their Products, and Cytokines, J. Immunol., 168:554-561 (Jan. 2002).

Kobe et al., Proteins with leucine-rich repeats, Current Opinion in Structural Biology 5:409-416 (Jun. 1995).

Modlin., Mammalian Toll-like receptors, Annals of Allergy, Asthma, & Immunology, 88:543-548 (Jun. 2002).

Heine et al., Toll-Like Receptors and Their Function in Innate and Adaptive Immunity, Int. Arch. Allergy Immunol., 130:180-192 (Mar. 2003).

Takeda et al., Toll-Like Receptors, Annu. Rev. Immunol. 21:335-376 (Dec. 2003).

Dunne et al., The Interleukin-1 Receptor/Toll-Like Receptor Superfamily, Science's STKE 2003 (171):re3 (Feb. 2003) (17 pages).

* cited by examiner

*Primary Examiner*—Amber D. Steele

(57) ABSTRACT

The present invention relates to novel screening methods for identifying agonists and antagonists of toll-like receptor (TLR) 7, TLR8 or TLR9. Methods are disclosed for identifying agonists and antagonists of TLR7, TLR8 or TLR9 using mutant TLR proteins containing deletions in one or more extracellular leucine rich regions (LRRs). Such agonists and antagonists have utility in the prevention, treatment and/or cure of various diseases and conditions, including cancer, virus infection, allergy, asthma, and chronic obstructive pulmonary disease (COPD).

3 Claims, 1 Drawing Sheet

Figure 1

| TLR LRR* | TLR7 |
|---|---|
| 1 | 66-89 |
| 2 | 90-127 |
| 3 | 128-148 |
| 4 | 149-172 |
| 5 | 173-204 |
| 6 | 205-225 |
| 7 | 226-249 |
| 8 | 250-290 |
| 9 | 291-314 |
| 10 | 315-340 |
| 11 | 341-370 |
| 12 | 371-397 |
| 13 | 398-421 |
| 14 | 422-444 |
| Undefined | 445-493 |
| 15 | 494-517 |
| 16 | 518-542 |
| 17 | 543-566 |
| 18 | 567-596 |
| 19 | 597-619 |
| 20 | 620-650 |
| 21 | 651-675 |
| 22 | 676-699 |
| 23 | 700-723 |
| 24 | 724-747 |
| 25 | 748-773 |
| C-Terminal Motif | 774-833 |

SCREENING ASSAY FOR TLR7, TLR8 AND TLR9 AGONISTS AND ANTAGONISTS

CROSS REFERENCE TO RELATED APPLICATIONS

This application claims priority benefit of U.S. provisional application No. 60/665,068, filed Mar. 24, 2005, which is incorporated by reference in its entirety.

FIELD OF THE INVENTION

The present invention relates to the field of screening methods for identification of compounds that potentiate immune response mechanisms to treat various diseases, such as cancer, virus infection, allergy, asthma, and chronic obstructive pulmonary disease (COPD).

BACKGROUND OF THE INVENTION

Toll-like receptors (TLRs) are type-I transmembrane proteins which are responsible for initiation of innate immune responses in vertebrates. They recognize a variety of pathogen-associated molecular patterns (PAMPS) from bacteria, viruses and fungi and act as a first line of defense against invading pathogens. There are ten human TLRs that elicit overlapping yet distinct biological responses due to differences in cellular expression and signaling pathways they initiate.

TLRs possess 19-25 contiguous copies of an extracellular N-terminal motif known as the leucine-rich repeat (LRR) motif, followed by a cysteine-rich region and an intracellular region. (Bell et al., *Trends Immunol.* 24:528 (2003)). The LRR region is a common feature among the TLRs and is important for ligand binding and cellular signaling. (Modlin, R. L., *Ann. Allergy Asthma Immunol.* 88:543 (2002); Kobe and Diesenhofer, *Curr. Opin. Struct. Biol.* 5:409 (1995)).

In humans, TLR7 is expressed mostly in human plasmocytoid dendritic cells (pDCs) and B cells. TLR8 is expressed mostly in cells of myeloid origin, i.e., monocytes, granulocytes and myeloid dendritic cells. TLR9, like TLR7, is expressed in B cells and dendritic cells. (Zarember and Godowski, *J. Immunol.* 168:554 (2002); Hornung et al., *J. Immunol.* 168:4 (2002); Rehli, *Trends Immunol.* 23:375 (2002).

TLR9, which appears to be localized intracellularly, is involved in the inflammatory response to bacterial DNA and oligonucleotides that contain unmethylated CpG sequences. (Shirota, H. et al., *J. Immunol.* 167:1882 (2001); Takeda, K. et al., *Annu. Rev. Immunol.* 21:335 (2003)). The role of TLR7, and of its close homologue TLR8, is to detect the presence of "foreign" single-stranded RNA within a cell, as a means to respond to viral invasion. (Heil et al., *Science* 303:1526 (2004); Diebold et al., *Science* 303:1529 (2004)). Single-stranded RNA derived from HIV-1 or the influenza virus was shown to induce the production of proinflammatory cytokines in pDCs. The distinguishing features of viral RNAs might be either their high U or G/U content, or the absence of a long poly-A tail at the 3' terminus of messenger RNA.

Certain compounds of the imidazoquinoline family, notably R848, act as agonists for TLR7 and TLR8. (Heine and Lein, *Int. Arch. Allergy Immunol.* 130:180 (2003); Dunne and O'Neill, *Sci. STKE* 2003:re3 (2003)). Once engaged, TLRs initiate a signal transduction cascade leading to activation of NFκB via the adapter protein myeloid differentiation primary response gene 88 (MyD88) and recruitment of the IL-1 receptor associated kinase (IRAK). Phosphorylation of IRAK then leads to recruitment of TNF-receptor associated factor 6 (TRAF6), which then results in the phosphorylation of the NFκB inhibitor I-κB. As a result, NFκB enters the cell nucleus and initiates transcription of genes whose promoters contain NFκB binding sites, such as cytokines (Singh et al., *Curr. Sci.* 85:1156 (2003)). Indeed, treatment of TLR8-expressing cells, such as PBMCs, with R848 results in production of high levels of IL-12, IFN-γ, IL-1, TNF-α, IL-6 and other inflammatory cytokines. Similarly, stimulation of TLR7-expressing cells, such as pDCs, results in production of very high levels of interferon-α and low levels of inflammatory cytokines.

Through activation of dendritic cells and other antigen-presenting cells, TLR7, TLR8 or TLR9 engagement and cytokine production is expected to activate diverse innate and acquired immune response mechanisms leading to the destruction of pathogens, infected cells or tumor cells. Thus, there is a need for agonists of TLR7, TLR8 or TLR9 for the treatment of cancer, virus infections, allergy, asthma, and COPD. TLR7, TLR8 or TLR9 and agonists thereof, however, require relatively high concentrations of compounds (in the double digit μg/ml range), and such concentrations are often difficult to achieve with complex chemical compounds due to solubility and/or cytotoxicity issues. As a result, screening is usually performed under conditions of low compound concentrations where possible agonists might not give activation levels readily detectable using standard cellular assays for screening. Thus, there is an immediate need for improved screening methods for identifying TLR7, TLR8 or TLR9 agonists.

SUMMARY OF THE INVENTION

The present invention fills the foregoing need by providing a screening method for identifying TLR7, TLR8 or TLR9 agonists and antagonists using low concentrations of compounds, as well as compositions and reagents for performing such a screening method. Applicants have found that mutant TLR7, TLR8 or TLR9 proteins comprising deletions in one or more LRRs makes these receptors more sensitive to low concentrations of agonists, thereby providing more efficient screening methods for identifying TLR7, TLR8 or TLR9 agonists and antagonists as compared to wild-type TLR7, TLR8 or TLR9 proteins.

Accordingly, one aspect of the present invention is directed to an isolated TLR7, TLR8 or TLR9 protein comprising deletions in one or more LRRs. Preferably, the TLR7, TLR8 or TLR9 protein comprises a deletion in the second LRR. In some embodiments, the TLR7 protein comprises the amino acid sequence set forth in SEQ ID NO: 2. In other embodiments, the TLR8 protein comprises the amino acid sequence set forth in SEQ ID NO: 6. In further embodiments, the TLR proteins lack their associated signal peptides.

Another aspect of the present invention is directed to an isolated nucleic acid sequence encoding a TLR7, TLR8 or TLR9 protein comprising deletions in one or more LRRs. Preferably, the nucleic acid sequence encodes a TLR7, TLR8 or TLR9 protein comprising a deletion in the second LRR. In some embodiments, the nucleic acid sequence encoding a TLR7 protein comprising deletions in one or more LRRs comprises the nucleotide sequence set forth in SEQ ID NO: 1. In other embodiments, the nucleic acid sequence encoding a TLR8 protein comprising deletions in one or more LRRs comprises the nucleotide sequence set for the in SEQ ID NO: 5.

Another aspect of the present invention is directed to a recombinant vector comprising a nucleic acid sequence encoding a TLR7, TLR8 or TLR9 protein comprising a deletion in one or more LRRs. Preferably, the recombinant vector is an expression vector in which the nucleic acid sequence is operably linked to a genetic control element capable of directing expression of the nucleic acid sequence in a host cell.

Another aspect of the present invention is directed to a host cell comprising a recombinant vector comprising a nucleic acid sequence encoding a TLR7, TLR8 or TLR9 protein comprising a deletion in one or more LRRS. The host cell can be prokaryotic or eukaryotic, but is preferably eukaryotic. In some embodiments, the host cell is a eukaryotic cell transiently transfected with a recombinant vector capable of directing expression of the TLR7, TLR8 or TLR9 protein comprising deletions in one or more LRRs. In other embodiments, the host cell is a eukaryotic cell stably transfected with the recombinant vector.

Another aspect of the present invention is directed to a method for producing a TLR7, TLR8 or TLR9 protein comprising a deletion in one or more LRRs comprising culturing a host cell comprising a recombinant vector comprising a nucleic acid molecule sequence encoding a TLR7, TLR8 or TLR9 protein comprising a deletion in one or more LRRs operably linked to a promoter sequence under conditions in which the nucleic acid sequence is expressed and TLR7, TLR8 or TLR9 protein comprising a deletion in one or more LRRs is produced. In some embodiments, the host cell is a transiently transfected eukaryotic cell. In other embodiments, the host cell is a stably transfected eukaryotic cell.

Another aspect of the present invention is directed to a screening method for identifying an agonist of TLR7, TLR8 or TLR9. According to one embodiment, the method comprises: (a) providing a host cell expressing NFκB comprising a recombinant expression vector comprising a nucleic acid sequence encoding a TLR7, TLR8 or TLR9 protein comprising a deletion in one or more LRRs; (b) culturing the host cell under conditions in which the nucleic acid sequence is expressed and TLR7, TLR8 or TLR9 protein comprising a deletion in one or more LRRs is produced; (c) contacting the host cell with a candidate agent to be tested for TLR7, TLR8 or TLR9 agonistic activity; and (d) measuring the level of an indicator of TLR7, TLR8 or TLR9 activation, whereby a TLR7, TLR8 or TLR9 agonist is identified by measurement of an increase in the level of indicator as compared to the level produced in the absence of such agonist. Preferably, the host cell is a eukaryotic cell. In some embodiments, the indicator is cytokine production. In other embodiments, the indicator is reporter molecule expression.

Another aspect of the present invention is directed to a screening method for identifying an antagonist of TLR7, TLR8 or TLR9. In one embodiment, the method comprises: (a) providing a host cell expressing NFκB comprising a recombinant expression vector comprising a nucleic acid sequence encoding a TLR7, TLR8 or TLR9 protein comprising a deletion in one or more LRRs; (b) culturing the host cell under conditions in which the nucleic acid sequence is expressed and TLR7, TLR8 or TLR9 protein comprising a deletion in one or more LRRs is produced; (c) contacting the host cell with a candidate agent to be tested for TLR7, TLR8 or TLR9 antagonistic activity in the presence of a known TLR7, TLR8 or TLR9 agonist; and (d) measuring the level of an indicator of TLR7, TLR8 or TLR9 activation, whereby a TLR7, TLR8 or TLR9 antagonist is identified by measurement of a decrease in the level of indicator as compared to the level produced in the absence of such antagonist. Preferably, the host cell is a eukaryotic cell. In some embodiments, the indicator is cytokine production. In other embodiments, the indicator is reporter expression.

An additional embodiment of the invention involves the use of an agonist or antagonist in the screening methods of the invention for the prevention or treatment of a disease.

BRIEF DESCRIPTION OF THE FIGS

FIG. 1 provides the location of leucine-rich repeats (LRRs) in TLR7. Residue ranges correspond to the Genbank sequence having accession number NP_057646 (SEQ ID NO: 4). Undefined refers to a region in TLR7 that contains no LRR or other known protein motif. The C-terminal (CT) motif ends at the last conserved Cys residue.

DETAILED DESCRIPTION OF THE INVENTION

The methods of the present invention can be performed utilizing routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

To aid in the understanding of the invention, the following non-limiting definitions are provided:

The term "agonist" refers to a compound that can combine with a TLR7, TLR8 or TLR9 receptor to produce or increase a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the TLR7, TLR8 or TLR9 receptor.

The term "activate", and variations thereof, refers to any measurable increase in cellular activity.

The term "antagonist" refers to a compound that can combine with a TLR7, TLR8 or TLR9 receptor to reduce or inhibit a cellular activity. An antagonist may be a ligand that directly binds to the receptor. Alternatively, an antagonist may combine with a receptor indirectly by, for example, (a) forming a complex with another molecule that directly binds to the receptor, or (b) otherwise results in the modification of another compound so that the other compound directly binds to the TLR7, TLR8 or TLR9 receptor.

The term "cellular activity" refers to a biological activity (e.g., cytokine production), that results from an agonist-receptor interaction.

The term "wild-type" refers to a nucleic acid or protein that has the characteristics of that nucleic acid or protein when isolated from a naturally occurring source. A wild-type nucleic acid or protein is that which is most frequently observed in a population and is thus arbitrarily designed the "normal" or "wild-type" form of that molecule. In contrast, the term "modified" or "mutant" refers to a nucleic acid or protein that displays modifications in sequence and/or functional properties (i.e., altered characteristics) when compared to the wild-type nucleic acid or protein.

The term "transfection" refers to the uptake of DNA by a cell. A cell has been "transfected" when exogenous (i.e., foreign) DNA has been introduced inside the cell membrane. Transfection can be either transient (i.e., the introduced DNA remains extrachromosomal and is diluted out during cell division) or stable (i.e., the introduced DNA integrates into the cell genome or is maintained as a stable episomal element).

"Co-transfection" refers to the simultaneous or sequential transfection of two or more nucleic acids or vectors into a given cell.

The terms "promoter element" or "promoter" refer to a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences.

The terms "in operable combination", "in operable order" or "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "selectable marker" or "selectable gene product" refer to the use of a nucleic acid sequence that encodes an enzymatic activity that confers resistance to an antibiotic or drug upon the cell in which the selectable marker is expressed. Selectable markers may be "positive"; positive selectable markers typically are dominant selectable markers, i.e., genes that encode an enzymatic activity that can be detected in a living cell or cell line. Selectable markers may also be "negative"; negative selectable markers encode an enzymatic activity (e.g., HSV thymidine kinase) whose expression is cytotoxic to the cell when grown in an appropriate selective medium (e.g., gancyclovir).

The term "vector" refers to a nucleic acid assembly capable of transferring gene sequences to target cells (e.g., viral vectors, non-viral vectors, particulate carriers, and liposomes). The term "expression vector" refers to a nucleic acid assembly containing a promoter that is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells. Thus, the term includes cloning and expression vehicles, as well as viral vectors.

The term "reporter gene" refers to a nucleotide sequence included in an expression vector that confers a detectable phenotype. For example, the reporter gene may cause expression of a "reporter molecule", which confers a detectable phenotype on a cell.

The term "agent" or "compound" describes any molecule, e.g. protein or pharmaceutical, that is screened for the capability of acting as an agonist or antagonist of TLR7, TLR8 or TLR9. An agent may also be identified as an agonist or antagonist by utilizing the screening methods of the invention.

The terms "treating" or "treatment" of a disease refer to executing a protocol, which may include administering one or more drugs to a patient (human or otherwise), in an effort to alleviate signs or symptoms of the disease. Thus, "treating" or "treatment" does not require complete alleviation of signs or symptoms, does not require a cure, and specifically includes protocols that have only a marginal effect on the patient.

Aspects of the present invention provide novel materials and methods useful for identifying TLR7, TLR8 or TLR9 agonists and antagonists. The present invention is based on applicants' discovery that mutant TLR7, TLR8 or TLR9 proteins comprising deletions in one or more LRRs makes these receptors more sensitive to low concentrations of agonists, thereby providing more efficient screening methods for identifying TLR7, TLR8 or TLR9 agonists as compared to wild-type TLR7, TLR8 or TLR9 proteins. Such agonists find use in potentiating immune response mechanisms to treat or prevent various diseases, such as cancer, virus infection, allergy, asthma, and chronic obstructive pulmonary disease (COPD).

In one or more embodiments, the TLR7, TLR8 or TLR9 mutation can delete any or all of the amino acids comprising one or more LRRs. Preferably, the deletion occurs in at least the second LRR. The numbering of LRRs in various TLRS, as well as their amino acid sequences, is set forth in, e.g., Bell et al., *Trends Immunol.* 24:528 (2003). The amino acid sequence of a TLR7 protein comprising a deletion in the second LRR comprises the amino acid sequence set forth in SEQ ID NO: 2. The amino acid sequence of a TLR8 protein comprising a deletion in the second LRR comprises the amino acid sequence set forth in SEQ ID NO: 6.

When expressed in cells, the mutant TLR7, TLR8 or TLR9 proteins comprising deletions in one or more LRRs will typically lack their associated signal peptides. For example, a TLR7 protein comprising a deletion in the second LRR can comprise the amino acid sequence set forth in SEQ ID NO: 2 lacking the first 25 amino acids. Similarly, a TLR8 protein comprising a deletion in the second LRR can comprise the amino acid sequence set forth in SEQ ID NO: 6 lacking the first 44 amino acids. Various predictive methods exist for determining the amino acid sequences of mature secretory proteins lacking their signal peptides, including weight matrix algorithms and neural networking (Chou, *Protein Engineering* 14:75 (2001), which can then be verified by experimental methods, such as, e.g., N-terminal sequencing of the purified mature TLR proteins.

The nucleic acid sequences encoding the mutant TLR7, TLR8 or TLR9 proteins can be produced using methods well known in the art, including chemical synthesis, site-directed mutagenesis and PCR. Nucleic acid sequences encoding wild-type TLR7 proteins from various species are publicly available from Genbank and include human (Acc. No. NM_016562), mouse (Acc. No. NM_133211), chimpanzee (Acc. No. NM_016562), chicken (Acc. No. XM_416836), rat (Acc. No. XM_228909), and dog (Acc. No. XM_548863). Nucleic acid sequences encoding wild-type TLR8 proteins from various species are also publicly available from Genbank and include human (Acc. Nos. NM_016610 and NM_138636), chimpanzee (Acc. No. XM_528893), pig (Acc. No. NM_214187), and mouse (Acc. No. NM_133212). Nucleic acid sequences encoding wild-type TLR9 proteins from various species are also publicly available from Genbank and include human (Acc. Nos. NM_017442 and NM_138688), rat (Acc. No. NM_198131), pig (Acc. No. NM_213958), dog (Acc. No. NM_001002998), cow (Acc. No. NM_183081), cat (Acc. No. AY137581) and mouse (Acc. No. NM_031178).

Allelic variants (SNPs, splice variants, translation initiation variants, etc.) and homologues (both paralogues and orthologues) of the sequences described above can also be used so long as they retain the desired structure and/or activity of TLR7, TLR8 or TLR9. For example, both human TLR8 and human TLR9 are each known to exist as two separate isoforms, a long form and short form. Methods for identifying homologous and allelic nucleic acid and amino acid sequences are well known in the art and include both hybridization-based and bioinformatics-based approaches (see Baxevanis and Ouellette, *Bioinformatics, A Practical Guide to the Analysis of Genes and Proteins* (2001)).

Preferably, the nucleic acid sequences are human in origin and encode a TLR protein comprising a deletion in the second LRR, such as those having amino acid sequences comprising the amino acid sequences set forth in SEQ ID NOs: 2 and 6. One such nucleic acid sequence encoding a TLR7 protein comprising a deletion in the second LRR comprises the nucleotide sequence set forth in SEQ ID NO: 1. One such nucleic acid sequence encoding a TLR8 protein comprising a deletion in the second LRR comprises the nucleotide sequence set for the in SEQ ID NO: 5. Due to the degeneracy of the genetic code, however, many different nucleotide sequences can encode the TLR proteins comprising the amino acid sequences set forth in SEQ ID NOs: 2 and 6. The codons can be selected for optimal expression in prokaryotic or eukaryotic systems.

For proper expression in cells, nucleic acid sequences encoding the mutant TLR7, TLR8 or TLR9 proteins will typically include nucleotides that encode an associated signal peptide. However, nucleic acid sequences lacking nucleotides that encode an associated signal peptide are also included within the scope of the invention. For example, a nucleic acid sequence encoding a TLR7 protein comprising a deletion in the second LRR can comprise the nucleotide sequence set forth in SEQ ID NO: 1 lacking the first 75 nucleotides. Similarly, a nucleic acid sequence encoding a TLR8 protein comprising a deletion in the second LRR can comprise the nucleotide sequence set forth in SEQ ID NO: 5 lacking the first 132 nucleotides. Again, due to the degeneracy of the genetic code, many different nucleotide sequences can encode the TLR proteins comprising the amino acid sequences set forth in SEQ ID NOs: 2 and 6 lacking their associated signal peptides.

Insertion of a nucleic acid sequence encoding a TLR7, TLR8 or TLR9 protein comprising a deletion in one or more LRRs into a vector is readily accomplished when the termini of the nucleic acid sequence and the vector comprise compatible restriction sites. If this cannot be done, it may be necessary to modify the termini of the nucleic acid and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated by the use of PCR. The cleaved vector and the DNA fragments may also be modified if required by homopolymeric tailing.

Recombinant expression vectors used in this invention are typically self-replicating DNA constructs comprising a nucleic acid sequence encoding a TLR7, TLR8 or TLR9 protein comprising a deletion in one or more LRRs operably linked to a suitable genetic control element that is capable of regulating expression of the nucleic acids in a compatible host cell. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Suitable prokaryotic promoters include the β-lactamase and lactose promoter systems, the tryptophan (trp) promoter system, the lambda PL promoter system and the tac promoter. Numerous expression vectors containing such control sequences are known in the art and available commercially. Suitable eukaryotic promoters include the cytomegalovirus (CMV) promoter, the SV40 early promoter region, the promoter contained in the 3' long terminal repeat of Rous sarcoma virus (RSV), the herpes TK promoter, the adenoviral promoter of an early or late (ElA, MLP, etc.) gene, the regulatory sequences of the metallothionein (MT) and phosphoglycerokinase (PGK) genes, as well as the TLR7, TLR8 or TLR9 promoters themselves. Inducible promoters and tissue specific promoters may also be used.

Suitable host cells for expressing a nucleic acid sequence encoding a TLR7, TLR8 or TLR9 protein comprising a deletion in one or more LRRs include prokaryotes and lower eukaryotes. Suitable prokaryotes include both gram negative and positive organisms, e.g., *E. coli* and *B. subtilis, S. typhimurium,* or any bacterial strain capable of expressing heterologous proteins. Suitable lower eukaryotes include yeast strains such *S. cerevisiae, S. pombe, Kluyveromyces* strains, *Candida*, or any yeast strain capable of expressing heterologous proteins. If the protein is made in yeast or bacteria, it may be necessary to modify the protein produced therein, for example by phosphorylation or glycosylation of the appropriate sites, or by introduction of the targeting sequences, in order to obtain a functional protein. Such covalent attachments may be accomplished using known chemical or enzymatic methods.

The host cell is preferably a higher eukaryote cell line. Suitable higher eukaryote cell lines include both primary and established cell lines from animal cells, both of non-mammalian origin, e.g., insect cells and birds, and of mammalian origin, e.g., human, primates, and rodents.

Higher eukaryotic tissue culture cells are preferred hosts for the recombinant production of a TLR7, TLR8 or TLR9 protein comprising a deletion in one or more LRRs. Although any higher eukaryotic tissue culture cell line might be used, including insect baculovirus expression systems, mammalian cells are preferred. Suitable mammalian cell lines include HeLa cells, Chinese hamster ovary (CHO) cells, baby rat kidney (BRK) cells, baby hamster kidney (BHK) cells, African green monkey kidney (COS and CV-1) cells, human embryonic kidney (HEK 293) cells, A431 cells, Colo2O5 cells, 3T3 cells, mouse L cells, HL-60 cells, U937 cells, HaK cells and Jurkat cells.

Methods for the transformation or transfection of such cells are well known in the art and include electroporation, calcium phosphate co-precipitation, protoplast or spheroplast fusion, lipofection, DEAE-dextran-mediated transfection, biolistics, and viral infection. The transfected expression vector can be maintained transiently in the cell. Alternatively, if the expression vector contains a selectable marker, cells can be selected in which the vector has stably integrated into the genome by culturing the transfected cells in the appropriate antibiotic or drug. Suitable dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin, and the bacterial xanthine-guanine phosphoribosyl transferase gene (also referred to as the gpt gene) which confers the ability to grow in the presence of mycophenolic acid.

Once transformed or transfected, the host cells can be cultured under conditions in which the nucleic acid sequence encoding a TLR7, TLR8 or TLR9 protein comprising a deletion in one or more LRRs is expressed and a TLR7, TLR8 or TLR9 protein comprising a deletion in one or more LRRs is produced. Generally, the resulting TLR protein will lack its associated signal peptide.

Host cells expressing a TLR7, TLR8 or TLR9 protein comprising a deletion in one or more LRRs find utility in screening methods for identifying agonists of TLR7, TLR8 or TLR9. As described below, a TLR7 or TLR8 protein comprising a deletion in the second LRR decreases 5-10 fold the agonist concentration required to achieve maximum activation levels of genes whose expression is induced by NFκB. These deletion mutants convey a significant advantage over the wild-type proteins because they can be used in screening assays to detect TLR7, TLR8 or TLR9 agonists in small compound concentrations, thereby avoiding solubility or cytotoxicity problems known to occur in solutions with a high concentration of compounds.

One embodiment of the agonist screening method involves (a) providing a host cell expressing NFκB comprising a nucleic acid sequence encoding a TLR7, TLR8 or TLR9 protein comprising a deletion in one or more LRRS; (b) culturing the host cell under conditions in which the recombinant nucleic acid molecule is expressed and TLR7, TLR8 or TLR9 protein comprising a deletion in one or more LRRs is produced; (c) contacting the host cell with a candidate agent to be tested for TLR7, TLR8 or TLR9 agonistic activity; and (d) measuring the level of an indicator of TLR7, TLR8 or TLR9 activation, whereby a TLR7, TLR8 or TLR9 agonist is identified by measurement of an increase in the level of indicator as compared to the level produced in the absence of such agonist.

Generally, a plurality of assays can be run in parallel with different agent concentrations to obtain a differential response to the various concentrations. Typically, one of these concentrations serves as a negative control, i.e., at zero concentration or below the level of detection. In addition, candidate agents are generally contacted with cells not expressing a TLR7, TLR8 or TLR9 protein comprising a deletion in one or more LRRs as a control for target specificity. Although the screening method generally is used as an assay to identify previously unknown molecules that can act as a therapeutic agent, the method can also be used to confirm and standardize the desired activity of a known TLR7, TLR8 or TLR9 agonist or to optimize the structure and/or activity of a known TLR7, TLR8 or TLR9 agonist during, e.g., molecular evolution procedures.

The indicator that is measured during the screening method can be an endogenous gene product whose expression is induced by NFκB, such as a cytokine. Such cytokines include IL-12, IFN-γ, IL-1, TNF-α, IL-6 and other inflammatory cytokines. Either the cytokine or the mRNA encoding the cytokine can be measured. Methods for measuring the levels of a cytokine or its mRNA are well known in the art and include, e.g., ELISA, RIA, Western blot, Northern blot, and quantitative PCR.

Alternatively, the indicator that is measured is a reporter molecule whose expression is induced by NFκB. Reporter assays are preferred because they are easily adaptable to high through-put screening procedures. Suitable reporter molecules include, for example, fluorescent polypeptides such as green fluorescent protein, cyan fluorescent protein, red fluorescent protein, or enhanced forms thereof; an antibiotic resistance polypeptide such as puromycin N-acetyltransferase, hygromycin B phosphotransferase, aminoglycoside phosphotransferase, and the Sh ble gene product; a cell surface protein marker such as the cell surface protein marker neural cell adhesion molecule (N-CAM); an enzyme such as β-lactamase, chloramphenicol acetyltransferase, adenosine deaminase, aminoglycoside phosphotransferase, dihydrofolate reductase, thymidine kinase, luciferase or xanthine guanine phosphoribosyltransferase polypeptide; or a tag such as a c-myc peptide, a polyhistidine, a FLAG epitope, or any ligand (or cognate receptor), including any peptide epitope (or antibody, or antigen binding fragment thereof, that specifically binds the epitope).

For example, a host cell expressing a TLR7, TLR8 or TLR9 protein comprising a deletion in one or more LRRs can be cotransfected with an expression vector comprising a luciferase gene operably linked to a genetic control element containing one or more NFκB binding sites (e.g., GGGGACTTTCC, SEQ ID NO: 19). Upon engagement of the TLR7, TLR8 or TLR9 deletion mutant by an agonist, NFκB will translocate into the cell nucleus and initiate transcription of the luciferase gene, resulting in expression of luciferase. Expression of luciferase can be detected and measured using the appropriate instrumentation and reagents, for example, by detecting light emission using a luminometer upon addition of luciferin.

Any candidate agent or compound can be screened in the above-described method. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to, peptides, saccharides, siRNA, antisense, antibodies, fatty acids, steroids, purines, pyrimidines, and various derivatives, structural analogs and combinations thereof.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Diseases and conditions amenable to treatment with the identified TLR7, TLR8 or TLR9 agonists are those in which an immune response is desired and include the following:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picomavirus (e.g., rhinovirus or enterovirus), an orthomyxovirus (e.g., influenza virus), a paramyxovirus (e.g., parainfluenza virus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, pneumocystis camii pneumonia, leishmaniasis, cryptosporidiosis, toxoplasmosis, and trypanosome infection; and (d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $TH_2$-mediated, atopic diseases, such as atopic dermatitis or eczema, eosinophilia, asthma, allergy, allergic rhinitis, COPD, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g, enhancing wound healing, including chronic wounds).

The screening method described above can also be used to identify antagonists of TLR7, TLR8 or TLR9. One embodiment of the antagonist screening method involves (a) providing a host cell expressing NFκB comprising a nucleic acid sequence encoding a TLR7, TLR8 or TLR9 protein comprising a deletion in one or more LRRs; (b) culturing the host cell under conditions in which the recombinant nucleic acid molecule is expressed and TLR7, TLR8 or TLR9 protein comprising a deletion in one or more LRRs is produced; (c) contacting the host cell with a candidate agent to be tested for TLR7, TLR8 or TLR9 antagonistic activity in the presence of a known TLR7, TLR8 or TLR9 agonist; and (d) measuring the level of an indicator of TLR7, TLR8 or TLR9 activation, whereby a TLR7, TLR8 or TLR9 antagonist is identified by measurement of a decrease in the level of indicator as compared to the level produced in the absence of such antagonist. Examples of known agonists of TLR7, TLR8 and TLR8 include R848, loxoribine, uridine, single-stranded viral RNA, and unmethylated bacterial DNA. Identified TLR7, TLR8 or TLR9 antagonists are expected to be useful in the treatment of inflammatory and autoimmune diseases.

Specific embodiments according to the methods of the present invention will now be described in the following examples. The examples are illustrative only, and are not intended to limit the remainder of the disclosure in any way.

EXAMPLES

Example 1

Construction of Human TLR7 and TLR8 Deletion Mutants

A nucleic acid sequence (comprising the nucleotide sequence set forth in SEQ ID NO: 1) encoding a mutant human TLR7 protein having a deletion of the amino acid sequence PIPLG (amino acids 102-106 of the wild-type human TLR7 amino acid sequence set forth in SEQ ID NO: 4) in the second LRR was prepared by PCR. Briefly, a first PCR was performed on the human wild-type TLR7 cDNA (SEQ ID NO: 3 cloned into the expression vector pCMVFlag (a derivative of pCR3.1 (Invitrogen, Carlsbad, Calif.)) (pCMVhuTLR7) using the sense primer 5'-CTA ACT AGA GAA CCC ACT GC-3' (SEQ ID NO: 9) and the antisense primer 5'-GAT GCA CAT GTT GTT TTT TGA TAC ACA GTT GCA TCT GAA ATC-3' (SEQ ID NO: 10). A second PCR was performed on the TLR7 cDNA using the sense primer 5'-GAT TTC AGA TGC AAC TGT GTA TCA AAA AAC AAC ATG TGC ATC-3' (SEQ ID NO: 11) and the antisense primer 5'-CTT CAC TTG AAT CTC CTG AAG-3' (SEQ ID NO: 12). The bands were gel purified and combined in a third PCR using the primers of SEQ ID NOs: 9 and 12. The band was gel purified, digested with BamHI and PmeI and cloned into pCMVhuTLR7 digested with the same enzymes to produce pCMVhuTLR7Δ2. The mutation was confirmed by DNA sequencing. The resulting mutant TLR7 amino acid sequence (comprising the amino acid sequence set forth in SEQ ID NO: 2) contained a FLAG epitope with an initiation methionine (MDYKDDDDK; SEQ ID NO: 18, encoded by 5'-ATG GAT TAC AAA GAC GAT GAC GAT AAA-3'; SEQ ID NO: 17) followed by a glutamic acid (E) and phenylalanine (F) upstream of the valine (V) at position 1 of SEQ ID NO: 2. The glutamic acid and phenylalanine residues were introduced by addition of an EcoRI restriction during construction of the wild-type pCMVhuTLR7 vector.

Similarly, a nucleic acid sequence (comprising the nucleotide sequence set forth in SEQ ID NO: 5) encoding a mutant TLR8 protein having a deletion of the amino acid sequence VQHQN (amino acids 118-122 of the wild-type human TLR8 isoform 1 amino acid sequence set forth in SEQ ID NO: 8) in the second LRR was prepared by PCR. Briefly, a first PCR was performed on the human wild-type TLR8 isoform 1 cDNA (SEQ ID NO: 7) cloned into the expression vector pcDNA™3.1/Zeo (Invitrogen) (pCMVhuTLR8) using the sense primer 5'-CTA ACT AGA GAA CCC ACT GC-3' (SEQ ID NO: 13) and the antisense primer 5'-GAT TGT ATA CCG GGA TTT CCA TTG GGG TTG TGG TTT AGA T-3' (SEQ ID NO: 14). A second PCR was performed on the TLR8 cDNA using the sense primer 5'-ATC TAA ACC ACA ACC CCA ATG GAA ATC CCG GTA TAC AAT C-3' (SEQ ID NO: 15) and the antisense primer 5'-ATC TTT TAC CAA CGG TGA TAT TCT G-3' (SEQ ID NO: 16). The bands were gel purified and combined in a third PCR using the primers of SEQ ID NOs: 13 and 16. The band was gel purified, digested with BamHI and ClaI or HindIII and ClaI and cloned into pCMVhuTLR8 digested with the same enzymes to produce pCMVhuTLR8Δ2. The mutation was confirmed by DNA sequencing. The resulting mutant TLR8 amino acid sequence (comprising the amino acid sequence set forth in SEQ ID NO: 6) contained a FLAG epitope with an initiation methionine (MDYKDDDDK; SEQ ID NO: 18, encoded by 5'-ATG GAT TAC AAA GAC GAT GAC GAT AAA-3'; SEQ ID NO: 17) upstream of the methionine (M) at position 1 of SEQ ID NO: 6. Alternatively, the shorter human wild-type TLR8 isoform 2 cDNA (Acc. No. NM_138636) can be used to produce a mutant TLR8 protein having a deletion of the amino acid sequence VQHQN (amino acids 100-104 of the wild-type human TLR8 isoform 2 amino acid sequence disclosed at Acc. No. NP_619542) in the second LRR.

A nucleic acid sequence encoding a human TLR9 protein having a deletion in the second LRR of the amino acid sequence PVGLS (e.g., amino acids 100-104 of the wild-type human TLR9 amino acid sequence disclosed at Acc. No. NP_059138 or amino acids 43-47 of the wild-type human TLR9 amino acid sequence disclosed at Acc. No. NP_619633) can be produced by similar methodologies using, e.g., cDNA encoding either the longer (NM_017442) or shorter (NM_138688) isoform of human TLR9, respectively.

Example 2

Expression and Activation of Human TLR7 and TLR8 Deletion Mutants

A comparison of the response of wild-type and mutant TLR7 and TLR8 proteins to agonist activation was performed. HEK 293 cells were transfected in bulk in 15 cm dishes with a mixture of NFκB-luciferase reporter plasmid (Clontech) and pCMVhuTLR7Δ2 or pCMVhuTLR8Δ2. Six hours after transfection, cells were divided into 96- or 384-well plates at different cell densities to achieve a degree of confluency between 25-100%. The next day, increasing concentrations of the TLR7 agonists R848, loxoribine, and uridine were added to the wells. Wells without agonist served as negative controls. After five hours, the cells were lysed with SteadyGlo™ luciferase reagent (Promega) according to the manufacturer's recommendations. After a 10-minute incubation period, luciferase activity was measured using a luminometer. The data were plotted as a fold-induction compared to luciferase activity of cells which received medium alone.

While 10 nM R848 did not result in significant activation of wild-type TLR7, mutant TLR7 containing a deletion in the second LRR mediated a reproducible 6-fold induction of luciferase activity. Close-to-maximum activation of wild-type TLR7 was achieved in the presence of 1 μM R848, while 10-fold lower concentrations were sufficient for full activation of the mutant TLR7. The weak TLR7 agonist loxoribine activated wild-type TLR7 only at levels greater than 0.5 mM, while the same activation was achieved with the mutant TLR7 at a 5-fold lower concentration of 0.1 mM.

Similarly, while at least 0.5 μM R848 was required to achieve 5-fold induction of luciferase with wild-type TLR8, 50 nm of R848 activated mutant TLR8 containing a deletion in the second LRR and stimulated close to 10-fold induction of luciferase. Additionally, 4.5 mM uridine activated mutant TLR8 15-fold, while in the presence of wild-type TLR8 only a marginal 3-fold activation was observed.

Thus, the described deletions in the second LRR of TLR7 and TLR8 increase the sensitivity of these receptors at least 5-10 fold compared to the wild-type receptors. As such, these mutant receptors provide screening methods that can more readily detect agonists and antagonists of TLR7, TLR8 and TLR9 and, therefore, will increase the probability of discovering new such molecules.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. An isolated mutant TLR7 protein comprising the amino acid sequence set forth in SEQ ID NO: 2.

2. The isolated mutant TLR7 protein of claim 1 lacking its associated signal peptide.

3. An isolated mutant TLR7 protein comprising the amino acid sequence set forth in residues 26-1043 of SEQ ID NO: 2.

* * * * *

SEQUENCE LISTING

```
<160> NUMBER OF SEQ ID NOS: 19

<210> SEQ ID NO 1
<211> LENGTH: 3132
<212> TYPE: DNA
<213> ORGANISM: Homo sapiens

<400> SEQUENCE: 1

gtgtttccaa tgtggacact gaagagacaa attcttatcc tttttaacat aatcctaatt     60

tccaaactcc ttggggctag atggtttcct aaaactctgc cctgtgatgt cactctggat    120

gttccaaaga accatgtgat cgtggactgc acagacaagc atttgacaga aattcctgga    180

ggtattccca cgaacaccac gaacctcacc ctcaccatta accacatacc agacatctcc    240

ccagcgtcct ttcacagact ggaccatctg gtagagatcg atttcagatg caactgtgta    300

tcaaaaaaca acatgtgcat caagaggctg cagattaaac ccagaagctt tagtggactc    360

acttatttaa aatcccttta cctggatgga aaccagctac tagagatacc gcagggcctc    420

ccgcctagct tacagcttct cagccttgag gccaacaaca tcttttccat cagaaaagag    480
```

-continued

```
aatctaacag aactggccaa catagaaata ctctacctgg gccaaaactg ttattatcga    540
aatccttgtt atgtttcata ttcaatagag aaagatgcct tcctaaactt gacaaagtta    600
aaagtgctct ccctgaaaga taacaatgtc acagccgtcc ctactgtttt gccatctact    660
ttaacagaac tatatctcta caacaacatg attgcaaaaa tccaagaaga tgattttaat    720
aacctcaacc aattacaaat tcttgaccta agtggaaatt gccctcgttg ttataatgcc    780
ccatttcctt gtgcgccgtg taaaaataat tctcccctac agatccctgt aaatgctttt    840
gatgcgctga cagaattaaa agttttacgt ctacacagta actctcttca gcatgtgccc    900
ccaagatggt ttaagaacat caacaaactc caggaactgg atctgtccca aaacttcttg    960
gccaaagaaa ttggggatgc taaatttctg cattttctcc ccagcctcat ccaattggat   1020
ctgtctttca attttgaact tcaggtctat cgtgcatcta tgaatctatc acaagcattt   1080
tcttcactga aaagcctgaa aattctgcgg atcagaggat atgtctttaa agagttgaaa   1140
agctttaacc tctcgccatt acataatctt caaaatcttg aagttcttga tcttggcact   1200
aactttataa aaattgctaa cctcagcatg tttaaacaat ttaaaagact gaaagtcata   1260
gatctttcag tgaataaaat atcaccttca ggagattcaa gtgaagttgg cttctgctca   1320
aatgccagaa cttctgtaga aagttatgaa ccccaggtcc tggaacaatt acattatttc   1380
agatatgata agtatgcaag gagttgcaga ttcaaaaaca aagaggcttc tttcatgtct   1440
gttaatgaaa gctgctacaa gtatgggcag accttggatc taagtaaaaa tagtatattt   1500
tttgtcaagt cctctgattt tcagcatctt tctttcctca aatgcctgaa tctgtcagga   1560
aatctcatta gccaaactct taatggcagt gaattccaac ctttagcaga gctgagatat   1620
ttggacttct ccaacaaccg gcttgattta ctccattcaa cagcatttga agagcttcac   1680
aaactggaag ttctggatat aagcagtaat agccattatt ttcaatcaga aggaattact   1740
catatgctaa actttaccaa gaacctaaag gttctgcaga aactgatgat gaacgacaat   1800
gacatctctt cctccaccag caggaccatg gagagtgagt ctcttagaac tctggaattc   1860
agaggaaatc acttagatgt tttatggaga gaaggtgata acagatactt acaattattc   1920
aagaatctgc taaaattaga ggaattagac atctctaaaa attccctaag tttcttgcct   1980
tctggagttt ttgatggtat gcctccaaat ctaaagaatc tctctttggc caaaaatggg   2040
ctcaaatctt tcagttggaa gaaactccag tgtctaaaga acctggaaac tttggacctc   2100
agccacaacc aactgaccac tgtccctgag agattatcca actgttccag aagcctcaag   2160
aatctgattc ttaagaataa tcaaatcagg agtctgacga agtattttct acaagatgcc   2220
ttccagttgc gatatctgga tctcagctca aataaaatcc agatgatcca aaagaccagc   2280
ttcccagaaa atgtcctcaa caatctgaag atgttgcttt tgcatcataa tcggtttctg   2340
tgcacctgtg atgctgtgtg gtttgtctgg tgggttaacc atacggaggt gactattcct   2400
tacctggcca cagatgtgac ttgtgtgggg ccaggagcac acaagggcca aagtgtgatc   2460
tccctggatc tgtacacctg tgagttagat ctgactaacc tgattctgtt ctcactttcc   2520
atatctgtat ctctctttct catggtgatg atgacagcaa gtcacctcta tttctgggat   2580
gtgtggtata tttaccattt ctgtaaggcc aagataaagg ggtatcagcg tctaatatca   2640
ccagactgtt gctatgatgc ttttattgtg tatgacacta aagacccagc tgtgaccgag   2700
tgggttttgg ctgagctggt ggccaaactg gaagacccaa gagagaaaca ttttaattta   2760
tgtctcgagg aaagggactg gttaccaggg cagccagttc tggaaaacct ttcccagagc   2820
```

-continued

```
atacagctta gcaaaaagac agtgtttgtg atgacagaca agtatgcaaa gactgaaaat   2880

tttaagatag cattttactt gtcccatcag aggctcatgg atgaaaaagt tgatgtgatt   2940

atcttgatat ttcttgagaa gccctttcag aagtccaagt tcctccagct ccggaaaagg   3000

ctctgtggga gttctgtcct tgagtggcca acaaacccgc aagctcaccc atacttctgg   3060

cagtgtctaa agaacgccct ggccacagac aatcatgtgg cctatagtca ggtgttcaag   3120

gaaacggtct ag                                                         3132


<210> SEQ ID NO 2
<211> LENGTH: 1043
<212> TYPE: PRT
<213> ORGANISM: Homo sapiens

<400> SEQUENCE: 2

Val Phe Pro Met Trp Thr Leu Lys Arg Gln Ile Leu Ile Leu Phe Asn
1               5                   10                  15

Ile Ile Leu Ile Ser Lys Leu Leu Gly Ala Arg Trp Phe Pro Lys Thr
            20                  25                  30

Leu Pro Cys Asp Val Thr Leu Asp Val Pro Lys Asn His Val Ile Val
        35                  40                  45

Asp Cys Thr Asp Lys His Leu Thr Glu Ile Pro Gly Gly Ile Pro Thr
    50                  55                  60

Asn Thr Thr Asn Leu Thr Leu Thr Ile Asn His Ile Pro Asp Ile Ser
65                  70                  75                  80

Pro Ala Ser Phe His Arg Leu Asp His Leu Val Glu Ile Asp Phe Arg
                85                  90                  95

Cys Asn Cys Val Ser Lys Asn Asn Met Cys Ile Lys Arg Leu Gln Ile
            100                 105                 110

Lys Pro Arg Ser Phe Ser Gly Leu Thr Tyr Leu Lys Ser Leu Tyr Leu
        115                 120                 125

Asp Gly Asn Gln Leu Leu Glu Ile Pro Gln Gly Leu Pro Pro Ser Leu
    130                 135                 140

Gln Leu Leu Ser Leu Glu Ala Asn Asn Ile Phe Ser Ile Arg Lys Glu
145                 150                 155                 160

Asn Leu Thr Glu Leu Ala Asn Ile Glu Ile Leu Tyr Leu Gly Gln Asn
                165                 170                 175

Cys Tyr Tyr Arg Asn Pro Cys Tyr Val Ser Tyr Ser Ile Glu Lys Asp
            180                 185                 190

Ala Phe Leu Asn Leu Thr Lys Leu Lys Val Leu Ser Leu Lys Asp Asn
        195                 200                 205

Asn Val Thr Ala Val Pro Thr Val Leu Pro Ser Thr Leu Thr Glu Leu
    210                 215                 220

Tyr Leu Tyr Asn Asn Met Ile Ala Lys Ile Gln Glu Asp Asp Phe Asn
225                 230                 235                 240

Asn Leu Asn Gln Leu Gln Ile Leu Asp Leu Ser Gly Asn Cys Pro Arg
                245                 250                 255

Cys Tyr Asn Ala Pro Phe Pro Cys Ala Pro Cys Lys Asn Asn Ser Pro
            260                 265                 270

Leu Gln Ile Pro Val Asn Ala Phe Asp Ala Leu Thr Glu Leu Lys Val
        275                 280                 285

Leu Arg Leu His Ser Asn Ser Leu Gln His Val Pro Pro Arg Trp Phe
    290                 295                 300

Lys Asn Ile Asn Lys Leu Gln Glu Leu Asp Leu Ser Gln Asn Phe Leu
305                 310                 315                 320
```

-continued

```
Ala Lys Glu Ile Gly Asp Ala Lys Phe Leu His Phe Leu Pro Ser Leu
                325                 330                 335

Ile Gln Leu Asp Leu Ser Phe Asn Phe Glu Leu Gln Val Tyr Arg Ala
            340                 345                 350

Ser Met Asn Leu Ser Gln Ala Phe Ser Ser Leu Lys Ser Leu Lys Ile
        355                 360                 365

Leu Arg Ile Arg Gly Tyr Val Phe Lys Glu Leu Lys Ser Phe Asn Leu
    370                 375                 380

Ser Pro Leu His Asn Leu Gln Asn Leu Glu Val Leu Asp Leu Gly Thr
385                 390                 395                 400

Asn Phe Ile Lys Ile Ala Asn Leu Ser Met Phe Lys Gln Phe Lys Arg
                405                 410                 415

Leu Lys Val Ile Asp Leu Ser Val Asn Lys Ile Ser Pro Ser Gly Asp
            420                 425                 430

Ser Ser Glu Val Gly Phe Cys Ser Asn Ala Arg Thr Ser Val Glu Ser
        435                 440                 445

Tyr Glu Pro Gln Val Leu Glu Gln Leu His Tyr Phe Arg Tyr Asp Lys
    450                 455                 460

Tyr Ala Arg Ser Cys Arg Phe Lys Asn Lys Glu Ala Ser Phe Met Ser
465                 470                 475                 480

Val Asn Glu Ser Cys Tyr Lys Tyr Gly Gln Thr Leu Asp Leu Ser Lys
                485                 490                 495

Asn Ser Ile Phe Phe Val Lys Ser Ser Asp Phe Gln His Leu Ser Phe
            500                 505                 510

Leu Lys Cys Leu Asn Leu Ser Gly Asn Leu Ile Ser Gln Thr Leu Asn
        515                 520                 525

Gly Ser Glu Phe Gln Pro Leu Ala Glu Leu Arg Tyr Leu Asp Phe Ser
    530                 535                 540

Asn Asn Arg Leu Asp Leu Leu His Ser Thr Ala Phe Glu Glu Leu His
545                 550                 555                 560

Lys Leu Glu Val Leu Asp Ile Ser Ser Asn Ser His Tyr Phe Gln Ser
                565                 570                 575

Glu Gly Ile Thr His Met Leu Asn Phe Thr Lys Asn Leu Lys Val Leu
            580                 585                 590

Gln Lys Leu Met Met Asn Asp Asn Asp Ile Ser Ser Ser Thr Ser Arg
        595                 600                 605

Thr Met Glu Ser Glu Ser Leu Arg Thr Leu Glu Phe Arg Gly Asn His
    610                 615                 620

Leu Asp Val Leu Trp Arg Glu Gly Asp Asn Arg Tyr Leu Gln Leu Phe
625                 630                 635                 640

Lys Asn Leu Leu Lys Leu Glu Glu Leu Asp Ile Ser Lys Asn Ser Leu
                645                 650                 655

Ser Phe Leu Pro Ser Gly Val Phe Asp Gly Met Pro Pro Asn Leu Lys
            660                 665                 670

Asn Leu Ser Leu Ala Lys Asn Gly Leu Lys Ser Phe Ser Trp Lys Lys
        675                 680                 685

Leu Gln Cys Leu Lys Asn Leu Glu Thr Leu Asp Leu Ser His Asn Gln
    690                 695                 700

Leu Thr Thr Val Pro Glu Arg Leu Ser Asn Cys Ser Arg Ser Leu Lys
705                 710                 715                 720

Asn Leu Ile Leu Lys Asn Asn Gln Ile Arg Ser Leu Thr Lys Tyr Phe
                725                 730                 735
```

-continued

```
Leu Gln Asp Ala Phe Gln Leu Arg Tyr Leu Asp Leu Ser Ser Asn Lys
            740                 745                 750

Ile Gln Met Ile Gln Lys Thr Ser Phe Pro Glu Asn Val Leu Asn Asn
        755                 760                 765

Leu Lys Met Leu Leu Leu His His Asn Arg Phe Leu Cys Thr Cys Asp
    770                 775                 780

Ala Val Trp Phe Val Trp Trp Val Asn His Thr Glu Val Thr Ile Pro
785                 790                 795                 800

Tyr Leu Ala Thr Asp Val Thr Cys Val Gly Pro Gly Ala His Lys Gly
                805                 810                 815

Gln Ser Val Ile Ser Leu Asp Leu Tyr Thr Cys Glu Leu Asp Leu Thr
            820                 825                 830

Asn Leu Ile Leu Phe Ser Leu Ser Ile Ser Val Ser Leu Phe Leu Met
        835                 840                 845

Val Met Met Thr Ala Ser His Leu Tyr Phe Trp Asp Val Trp Tyr Ile
    850                 855                 860

Tyr His Phe Cys Lys Ala Lys Ile Lys Gly Tyr Gln Arg Leu Ile Ser
865                 870                 875                 880

Pro Asp Cys Cys Tyr Asp Ala Phe Ile Val Tyr Asp Thr Lys Asp Pro
                885                 890                 895

Ala Val Thr Glu Trp Val Leu Ala Glu Leu Val Ala Lys Leu Glu Asp
            900                 905                 910

Pro Arg Glu Lys His Phe Asn Leu Cys Leu Glu Glu Arg Asp Trp Leu
        915                 920                 925

Pro Gly Gln Pro Val Leu Glu Asn Leu Ser Gln Ser Ile Gln Leu Ser
    930                 935                 940

Lys Lys Thr Val Phe Val Met Thr Asp Lys Tyr Ala Lys Thr Glu Asn
945                 950                 955                 960

Phe Lys Ile Ala Phe Tyr Leu Ser His Gln Arg Leu Met Asp Glu Lys
                965                 970                 975

Val Asp Val Ile Ile Leu Ile Phe Leu Glu Lys Pro Phe Gln Lys Ser
            980                 985                 990

Lys Phe Leu Gln Leu Arg Lys Arg  Leu Cys Gly Ser Ser  Val Leu Glu
        995                 1000                1005

Trp Pro  Thr Asn Pro Gln Ala  His Pro Tyr Phe Trp  Gln Cys Leu
    1010                1015                1020

Lys Asn  Ala Leu Ala Thr Asp  Asn His Val Ala Tyr  Ser Gln Val
    1025                1030                1035

Phe Lys  Glu Thr Val
    1040
```

```
<210> SEQ ID NO 3
<211> LENGTH: 3418
<212> TYPE: DNA
<213> ORGANISM: Homo sapiens
<220> FEATURE:
<221> NAME/KEY: CDS
<222> LOCATION: (136)..(3285)

<400> SEQUENCE: 3

actccagata taggatcact ccatgccatc aagaaagttg atgctattgg gcccatctca     60

agctgatctt ggcacctctc atgctctgct ctcttcaacc agacctctac attccatttt    120

ggaagaagac taaaa atg gtg ttt cca atg tgg aca ctg aag aga caa att     171
                 Met Val Phe Pro Met Trp Thr Leu Lys Arg Gln Ile
                 1               5                   10
```

-continued

```
ctt atc ctt ttt aac ata atc cta att tcc aaa ctc ctt ggg gct aga      219
Leu Ile Leu Phe Asn Ile Ile Leu Ile Ser Lys Leu Leu Gly Ala Arg
        15                  20                  25

tgg ttt cct aaa act ctg ccc tgt gat gtc act ctg gat gtt cca aag      267
Trp Phe Pro Lys Thr Leu Pro Cys Asp Val Thr Leu Asp Val Pro Lys
    30                  35                  40

aac cat gtg atc gtg gac tgc aca gac aag cat ttg aca gaa att cct      315
Asn His Val Ile Val Asp Cys Thr Asp Lys His Leu Thr Glu Ile Pro
45                  50                  55                  60

gga ggt att ccc acg aac acc acg aac ctc acc ctc acc att aac cac      363
Gly Gly Ile Pro Thr Asn Thr Thr Asn Leu Thr Leu Thr Ile Asn His
                65                  70                  75

ata cca gac atc tcc cca gcg tcc ttt cac aga ctg gac cat ctg gta      411
Ile Pro Asp Ile Ser Pro Ala Ser Phe His Arg Leu Asp His Leu Val
            80                  85                  90

gag atc gat ttc aga tgc aac tgt gta cct att cca ctg ggg tca aaa      459
Glu Ile Asp Phe Arg Cys Asn Cys Val Pro Ile Pro Leu Gly Ser Lys
        95                  100                 105

aac aac atg tgc atc aag agg ctg cag att aaa ccc aga agc ttt agt      507
Asn Asn Met Cys Ile Lys Arg Leu Gln Ile Lys Pro Arg Ser Phe Ser
    110                 115                 120

gga ctc act tat tta aaa tcc ctt tac ctg gat gga aac cag cta cta      555
Gly Leu Thr Tyr Leu Lys Ser Leu Tyr Leu Asp Gly Asn Gln Leu Leu
125                 130                 135                 140

gag ata ccg cag ggc ctc ccg cct agc tta cag ctt ctc agc ctt gag      603
Glu Ile Pro Gln Gly Leu Pro Pro Ser Leu Gln Leu Leu Ser Leu Glu
                145                 150                 155

gcc aac aac atc ttt tcc atc aga aaa gag aat cta aca gaa ctg gcc      651
Ala Asn Asn Ile Phe Ser Ile Arg Lys Glu Asn Leu Thr Glu Leu Ala
            160                 165                 170

aac ata gaa ata ctc tac ctg ggc caa aac tgt tat tat cga aat cct      699
Asn Ile Glu Ile Leu Tyr Leu Gly Gln Asn Cys Tyr Tyr Arg Asn Pro
        175                 180                 185

tgt tat gtt tca tat tca ata gag aaa gat gcc ttc cta aac ttg aca      747
Cys Tyr Val Ser Tyr Ser Ile Glu Lys Asp Ala Phe Leu Asn Leu Thr
    190                 195                 200

aag tta aaa gtg ctc tcc ctg aaa gat aac aat gtc aca gcc gtc cct      795
Lys Leu Lys Val Leu Ser Leu Lys Asp Asn Asn Val Thr Ala Val Pro
205                 210                 215                 220

act gtt ttg cca tct act tta aca gaa cta tat ctc tac aac aac atg      843
Thr Val Leu Pro Ser Thr Leu Thr Glu Leu Tyr Leu Tyr Asn Asn Met
                225                 230                 235

att gca aaa atc caa gaa gat gat ttt aat aac ctc aac caa tta caa      891
Ile Ala Lys Ile Gln Glu Asp Asp Phe Asn Asn Leu Asn Gln Leu Gln
            240                 245                 250

att ctt gac cta agt gga aat tgc cct cgt tgt tat aat gcc cca ttt      939
Ile Leu Asp Leu Ser Gly Asn Cys Pro Arg Cys Tyr Asn Ala Pro Phe
        255                 260                 265

cct tgt gcg ccg tgt aaa aat aat tct ccc cta cag atc cct gta aat      987
Pro Cys Ala Pro Cys Lys Asn Asn Ser Pro Leu Gln Ile Pro Val Asn
    270                 275                 280

gct ttt gat gcg ctg aca gaa tta aaa gtt tta cgt cta cac agt aac     1035
Ala Phe Asp Ala Leu Thr Glu Leu Lys Val Leu Arg Leu His Ser Asn
285                 290                 295                 300

tct ctt cag cat gtg ccc cca aga tgg ttt aag aac atc aac aaa ctc     1083
Ser Leu Gln His Val Pro Pro Arg Trp Phe Lys Asn Ile Asn Lys Leu
                305                 310                 315

cag gaa ctg gat ctg tcc caa aac ttc ttg gcc aaa gaa att ggg gat     1131
Gln Glu Leu Asp Leu Ser Gln Asn Phe Leu Ala Lys Glu Ile Gly Asp
            320                 325                 330
```

-continued

```
gct aaa ttt ctg cat ttt ctc ccc agc ctc atc caa ttg gat ctg tct      1179
Ala Lys Phe Leu His Phe Leu Pro Ser Leu Ile Gln Leu Asp Leu Ser
        335                 340                 345

ttc aat ttt gaa ctt cag gtc tat cgt gca tct atg aat cta tca caa      1227
Phe Asn Phe Glu Leu Gln Val Tyr Arg Ala Ser Met Asn Leu Ser Gln
    350                 355                 360

gca ttt tct tca ctg aaa agc ctg aaa att ctg cgg atc aga gga tat      1275
Ala Phe Ser Ser Leu Lys Ser Leu Lys Ile Leu Arg Ile Arg Gly Tyr
365                 370                 375                 380

gtc ttt aaa gag ttg aaa agc ttt aac ctc tcg cca tta cat aat ctt      1323
Val Phe Lys Glu Leu Lys Ser Phe Asn Leu Ser Pro Leu His Asn Leu
                385                 390                 395

caa aat ctt gaa gtt ctt gat ctt ggc act aac ttt ata aaa att gct      1371
Gln Asn Leu Glu Val Leu Asp Leu Gly Thr Asn Phe Ile Lys Ile Ala
            400                 405                 410

aac ctc agc atg ttt aaa caa ttt aaa aga ctg aaa gtc ata gat ctt      1419
Asn Leu Ser Met Phe Lys Gln Phe Lys Arg Leu Lys Val Ile Asp Leu
        415                 420                 425

tca gtg aat aaa ata tca cct tca gga gat tca agt gaa gtt ggc ttc      1467
Ser Val Asn Lys Ile Ser Pro Ser Gly Asp Ser Ser Glu Val Gly Phe
    430                 435                 440

tgc tca aat gcc aga act tct gta gaa agt tat gaa ccc cag gtc ctg      1515
Cys Ser Asn Ala Arg Thr Ser Val Glu Ser Tyr Glu Pro Gln Val Leu
445                 450                 455                 460

gaa caa tta cat tat ttc aga tat gat aag tat gca agg agt tgc aga      1563
Glu Gln Leu His Tyr Phe Arg Tyr Asp Lys Tyr Ala Arg Ser Cys Arg
                465                 470                 475

ttc aaa aac aaa gag gct tct ttc atg tct gtt aat gaa agc tgc tac      1611
Phe Lys Asn Lys Glu Ala Ser Phe Met Ser Val Asn Glu Ser Cys Tyr
            480                 485                 490

aag tat ggg cag acc ttg gat cta agt aaa aat agt ata ttt ttt gtc      1659
Lys Tyr Gly Gln Thr Leu Asp Leu Ser Lys Asn Ser Ile Phe Phe Val
        495                 500                 505

aag tcc tct gat ttt cag cat ctt tct ttc ctc aaa tgc ctg aat ctg      1707
Lys Ser Ser Asp Phe Gln His Leu Ser Phe Leu Lys Cys Leu Asn Leu
    510                 515                 520

tca gga aat ctc att agc caa act ctt aat ggc agt gaa ttc caa cct      1755
Ser Gly Asn Leu Ile Ser Gln Thr Leu Asn Gly Ser Glu Phe Gln Pro
525                 530                 535                 540

tta gca gag ctg aga tat ttg gac ttc tcc aac aac cgg ctt gat tta      1803
Leu Ala Glu Leu Arg Tyr Leu Asp Phe Ser Asn Asn Arg Leu Asp Leu
                545                 550                 555

ctc cat tca aca gca ttt gaa gag ctt cac aaa ctg gaa gtt ctg gat      1851
Leu His Ser Thr Ala Phe Glu Glu Leu His Lys Leu Glu Val Leu Asp
            560                 565                 570

ata agc agt aat agc cat tat ttt caa tca gaa gga att act cat atg      1899
Ile Ser Ser Asn Ser His Tyr Phe Gln Ser Glu Gly Ile Thr His Met
        575                 580                 585

cta aac ttt acc aag aac cta aag gtt ctg cag aaa ctg atg atg aac      1947
Leu Asn Phe Thr Lys Asn Leu Lys Val Leu Gln Lys Leu Met Met Asn
    590                 595                 600

gac aat gac atc tct tcc tcc acc agc agg acc atg gag agt gag tct      1995
Asp Asn Asp Ile Ser Ser Ser Thr Ser Arg Thr Met Glu Ser Glu Ser
605                 610                 615                 620

ctt aga act ctg gaa ttc aga gga aat cac tta gat gtt tta tgg aga      2043
Leu Arg Thr Leu Glu Phe Arg Gly Asn His Leu Asp Val Leu Trp Arg
                625                 630                 635

gaa ggt gat aac aga tac tta caa tta ttc aag aat ctg cta aaa tta      2091
Glu Gly Asp Asn Arg Tyr Leu Gln Leu Phe Lys Asn Leu Leu Lys Leu
```

-continued

```
        640                 645                 650

gag gaa tta gac atc tct aaa aat tcc cta agt ttc ttg cct tct gga     2139
Glu Glu Leu Asp Ile Ser Lys Asn Ser Leu Ser Phe Leu Pro Ser Gly
    655                 660                 665

gtt ttt gat ggt atg cct cca aat cta aag aat ctc tct ttg gcc aaa     2187
Val Phe Asp Gly Met Pro Pro Asn Leu Lys Asn Leu Ser Leu Ala Lys
670                 675                 680

aat ggg ctc aaa tct ttc agt tgg aag aaa ctc cag tgt cta aag aac     2235
Asn Gly Leu Lys Ser Phe Ser Trp Lys Lys Leu Gln Cys Leu Lys Asn
685                 690                 695                 700

ctg gaa act ttg gac ctc agc cac aac caa ctg acc act gtc cct gag     2283
Leu Glu Thr Leu Asp Leu Ser His Asn Gln Leu Thr Thr Val Pro Glu
                705                 710                 715

aga tta tcc aac tgt tcc aga agc ctc aag aat ctg att ctt aag aat     2331
Arg Leu Ser Asn Cys Ser Arg Ser Leu Lys Asn Leu Ile Leu Lys Asn
            720                 725                 730

aat caa atc agg agt ctg acg aag tat ttt cta caa gat gcc ttc cag     2379
Asn Gln Ile Arg Ser Leu Thr Lys Tyr Phe Leu Gln Asp Ala Phe Gln
        735                 740                 745

ttg cga tat ctg gat ctc agc tca aat aaa atc cag atg atc caa aag     2427
Leu Arg Tyr Leu Asp Leu Ser Ser Asn Lys Ile Gln Met Ile Gln Lys
    750                 755                 760

acc agc ttc cca gaa aat gtc ctc aac aat ctg aag atg ttg ctt ttg     2475
Thr Ser Phe Pro Glu Asn Val Leu Asn Asn Leu Lys Met Leu Leu Leu
765                 770                 775                 780

cat cat aat cgg ttt ctg tgc acc tgt gat gct gtg tgg ttt gtc tgg     2523
His His Asn Arg Phe Leu Cys Thr Cys Asp Ala Val Trp Phe Val Trp
                785                 790                 795

tgg gtt aac cat acg gag gtg act att cct tac ctg gcc aca gat gtg     2571
Trp Val Asn His Thr Glu Val Thr Ile Pro Tyr Leu Ala Thr Asp Val
            800                 805                 810

act tgt gtg ggg cca gga gca cac aag ggc caa agt gtg atc tcc ctg     2619
Thr Cys Val Gly Pro Gly Ala His Lys Gly Gln Ser Val Ile Ser Leu
        815                 820                 825

gat ctg tac acc tgt gag tta gat ctg act aac ctg att ctg ttc tca     2667
Asp Leu Tyr Thr Cys Glu Leu Asp Leu Thr Asn Leu Ile Leu Phe Ser
    830                 835                 840

ctt tcc ata tct gta tct ctc ttt ctc atg gtg atg atg aca gca agt     2715
Leu Ser Ile Ser Val Ser Leu Phe Leu Met Val Met Met Thr Ala Ser
845                 850                 855                 860

cac ctc tat ttc tgg gat gtg tgg tat att tac cat ttc tgt aag gcc     2763
His Leu Tyr Phe Trp Asp Val Trp Tyr Ile Tyr His Phe Cys Lys Ala
                865                 870                 875

aag ata aag ggg tat cag cgt cta ata tca cca gac tgt tgc tat gat     2811
Lys Ile Lys Gly Tyr Gln Arg Leu Ile Ser Pro Asp Cys Cys Tyr Asp
            880                 885                 890

gct ttt att gtg tat gac act aaa gac cca gct gtg acc gag tgg gtt     2859
Ala Phe Ile Val Tyr Asp Thr Lys Asp Pro Ala Val Thr Glu Trp Val
        895                 900                 905

ttg gct gag ctg gtg gcc aaa ctg gaa gac cca aga gag aaa cat ttt     2907
Leu Ala Glu Leu Val Ala Lys Leu Glu Asp Pro Arg Glu Lys His Phe
    910                 915                 920

aat tta tgt ctc gag gaa agg gac tgg tta cca ggg cag cca gtt ctg     2955
Asn Leu Cys Leu Glu Glu Arg Asp Trp Leu Pro Gly Gln Pro Val Leu
925                 930                 935                 940

gaa aac ctt tcc cag agc ata cag ctt agc aaa aag aca gtg ttt gtg     3003
Glu Asn Leu Ser Gln Ser Ile Gln Leu Ser Lys Lys Thr Val Phe Val
                945                 950                 955

atg aca gac aag tat gca aag act gaa aat ttt aag ata gca ttt tac     3051
```

-continued

```
Met Thr Asp Lys Tyr Ala Lys Thr Glu Asn Phe Lys Ile Ala Phe Tyr
            960                 965                 970

ttg tcc cat cag agg ctc atg gat gaa aaa gtt gat gtg att atc ttg     3099
Leu Ser His Gln Arg Leu Met Asp Glu Lys Val Asp Val Ile Ile Leu
        975                 980                 985

ata ttt ctt gag aag ccc ttt cag aag tcc aag ttc  ctc cag ctc cgg    3147
Ile Phe Leu Glu Lys Pro Phe Gln Lys Ser Lys Phe  Leu Gln Leu Arg
    990                 995                 1000

aaa  agg ctc tgt ggg agt  tct gtc ctt gag tgg  cca aca aac ccg      3192
Lys  Arg Leu Cys Gly Ser  Ser Val Leu Glu Trp  Pro Thr Asn Pro
1005                 1010                 1015

caa  gct cac cca tac ttc  tgg cag tgt cta aag  aac gcc ctg gcc      3237
Gln  Ala His Pro Tyr Phe  Trp Gln Cys Leu Lys  Asn Ala Leu Ala
1020                 1025                 1030

aca  gac aat cat gtg gcc  tat agt cag gtg ttc  aag gaa acg gtc      3282
Thr  Asp Asn His Val Ala  Tyr Ser Gln Val Phe  Lys Glu Thr Val
1035                 1040                 1045

tag ccccttctttg caaaacacaa ctgcctagtt taccaaggag aggcctggct         3335

gtttaaattg ttttcatata tatcacacca aaagcgtgtt ttgaaattct tcaagaaatg   3395

agattgccca tatttcaggg gag                                           3418


<210> SEQ ID NO 4
<211> LENGTH: 1049
<212> TYPE: PRT
<213> ORGANISM: Homo sapiens

<400> SEQUENCE: 4

Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220
```

-continued

```
Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
            340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu His
    450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
    610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
```

-continued

```
                645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
    690                 695                 700

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
    770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
    850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
    930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Ile Leu Ile Phe Leu Glu
            980                 985                 990

Lys Pro Phe Gln Lys Ser Lys Phe  Leu Gln Leu Arg Lys  Arg Leu Cys
        995                 1000                1005

Gly Ser  Ser Val Leu Glu Trp  Pro Thr Asn Pro Gln  Ala His Pro
    1010                1015                1020

Tyr Phe  Trp Gln Cys Leu Lys  Asn Ala Leu Ala Thr  Asp Asn His
    1025                1030                1035

Val Ala  Tyr Ser Gln Val Phe  Lys Glu Thr Val
    1040                1045
```

<210> SEQ ID NO 5

-continued

<211> LENGTH: 3165
<212> TYPE: DNA
<213> ORGANISM: Homo sapiens

<400> SEQUENCE: 5

```
atgaaggagt catctttgca aaatagctcc tgcagcctgg gaaaggagac taaaaaggaa     60

aacatgttcc tcgagtcgtc aatgctgacc tgcattttcc tgctaatatc tggttcctgt    120

gagttatgcg ccgaagaaaa tttttctaga agctatcctt gtgatgagaa aaagcaaaat    180

gactcagtta ttgcagagtg cagcaatcgt cgactacagg aagttcccca aacggtgggc    240

aaatatgtga cagaactaga cctgtctgat aatttcatca cacacataac gaatgaatca    300

tttcaagggc tgcaaaatct cactaaaata aatctaaacc acaaccccaa tggaaatccc    360

ggtatacaat caaatggctt gaatatcaca gacggggcat tcctcaacct aaaaaaccta    420

agggagttac tgcttgaaga caaccagtta ccccaaatac cctctggttt gccagagtct    480

ttgacagaac ttagtctaat tcaaaacaat atatacaaca taactaaaga gggcatttca    540

agacttataa acttgaaaaa tctctatttg gcctggaact gctattttaa caaagtttgc    600

gagaaaacta acatagaaga tggagtattt gaaacgctga caaatttgga gttgctatca    660

ctatctttca attctctttc acacgtgcca cccaaactgc caagctccct acgcaaactt    720

tttctgagca acacccagat caaatacatt agtgaagaag atttcaaggg attgataaat    780

ttaacattac tagatttaag cgggaactgt ccgaggtgct tcaatgcccc atttccatgc    840

gtgccttgtg atggtggtgc ttcaattaat atagatcgtt ttgcttttca aaacttgacc    900

caacttcgat acctaaacct ctctagcact tccctcagga agattaatgc tgcctggttt    960

aaaaatatgc ctcatctgaa ggtgctggat cttgaattca actatttagt gggagaaata   1020

gcctctgggg catttttaac gatgctgccc cgcttagaaa tacttgactt gtcttttaac   1080

tatataaagg ggagttatcc acagcatatt aatatttcca gaaacttctc taaacttttg   1140

tctctacggg cattgcattt aagaggttat gtgttccagg aactcagaga agatgatttc   1200

cagcccctga tgcagcttcc aaacttatcg actatcaact tgggtattaa ttttattaag   1260

caaatcgatt tcaaactttt ccaaaatttc tccaatctgg aaattattta cttgtcagaa   1320

aacagaatat caccgttggt aaaagatacc cggcagagtt atgcaaatag ttcctctttt   1380

caacgtcata tccggaaacg acgctcaaca gattttgagt ttgacccaca ttcgaacttt   1440

tatcatttca cccgtccttt aataaagcca caatgtgctg cttatggaaa agccttagat   1500

ttaagcctca acagtatttt cttcattggg ccaaaccaat ttgaaaatct tcctgacatt   1560

gcctgtttaa atctgtctgc aaatagcaat gctcaagtgt taagtggaac tgaattttca   1620

gccattcctc atgtcaaata tttggatttg acaaacaata gactagactt tgataatgct   1680

agtgctctta ctgaattgtc cgacttggaa gttctagatc tcagctataa ttcacactat   1740

ttcagaatag caggcgtaac acatcatcta gaatttattc aaaatttcac aaatctaaaa   1800

gttttaaact tgagccacaa caacatttat actttaacag ataagtataa cctggaaagc   1860

aagtccctgg tagaattagt tttcagtggc aatcgccttg acattttgtg gaatgatgat   1920

gacaacaggt atatctccat tttcaaaggt ctcaagaatc tgacacgtct ggatttatcc   1980

cttaataggc tgaagcacat cccaaatgaa gcattcctta atttgccagc gagtctcact   2040

gaactacata taaatgataa tatgttaaag tttttttaact ggacattact ccagcagttt   2100

cctcgtctcg agttgcttga cttacgtgga aacaaactac tctttttaac tgatagccta   2160

tctgacttta catcttccct tcggacactg ctgctgagtc ataacaggat ttcccaccta   2220
```

```
ccctctggct ttctttctga agtcagtagt ctgaagcacc tcgatttaag ttccaatctg   2280

ctaaaaacaa tcaacaaatc cgcacttgaa actaagacca ccaccaaatt atctatgttg   2340

gaactacacg gaaacccctt tgaatgcacc tgtgacattg gagatttccg aagatggatg   2400

gatgaacatc tgaatgtcaa aattcccaga ctggtagatg tcatttgtgc cagtcctggg   2460

gatcaaagag ggaagagtat tgtgagtctg gagctaacaa cttgtgtttc agatgtcact   2520

gcagtgatat tatttttctt cacgttcttt atcaccacca tggttatgtt ggctgccctg   2580

gctcaccatt tgttttactg ggatgtttgg tttatatata atgtgtgttt agctaaggta   2640

aaaggctaca ggtctctttc cacatcccaa actttctatg atgcttacat ttcttatgac   2700

accaaagatg cctctgttac tgactgggtg ataaatgagc tgcgctacca ccttgaagag   2760

agccgagaca aaaacgttct cctttgtcta gaggagaggg attgggaccc gggattggcc   2820

atcatcgaca acctcatgca gagcatcaac caaagcaaga aaacagtatt tgttttaacc   2880

aaaaaatatg caaaaagctg gaactttaaa acagcttttt acttggcttt gcagaggcta   2940

atggatgaga acatggatgt gattatattt atcctgctgg agccagtgtt acagcattct   3000

cagtatttga ggctacggca gcggatctgt aagagctcca tcctccagtg gcctgacaac   3060

ccgaaggcag aaggcttgtt ttggcaaact ctgagaaatg tggtcttgac tgaaaatgat   3120

tcacggtata acaatatgta tgtcgattcc attaagcaat actaa                   3165
```

<210> SEQ ID NO 6
<211> LENGTH: 1054
<212> TYPE: PRT
<213> ORGANISM: Homo sapiens

<400> SEQUENCE: 6

```
Met Lys Glu Ser Ser Leu Gln Asn Ser Ser Cys Ser Leu Gly Lys Glu
1               5                   10                  15

Thr Lys Lys Glu Asn Met Phe Leu Glu Ser Ser Met Leu Thr Cys Ile
            20                  25                  30

Phe Leu Leu Ile Ser Gly Ser Cys Glu Leu Cys Ala Glu Glu Asn Phe
        35                  40                  45

Ser Arg Ser Tyr Pro Cys Asp Glu Lys Lys Gln Asn Asp Ser Val Ile
    50                  55                  60

Ala Glu Cys Ser Asn Arg Arg Leu Gln Glu Val Pro Gln Thr Val Gly
65                  70                  75                  80

Lys Tyr Val Thr Glu Leu Asp Leu Ser Asp Asn Phe Ile Thr His Ile
                85                  90                  95

Thr Asn Glu Ser Phe Gln Gly Leu Gln Asn Leu Thr Lys Ile Asn Leu
            100                 105                 110

Asn His Asn Pro Asn Gly Asn Pro Gly Ile Gln Ser Asn Gly Leu Asn
        115                 120                 125

Ile Thr Asp Gly Ala Phe Leu Asn Leu Lys Asn Leu Arg Glu Leu Leu
    130                 135                 140

Leu Glu Asp Asn Gln Leu Pro Gln Ile Pro Ser Gly Leu Pro Glu Ser
145                 150                 155                 160

Leu Thr Glu Leu Ser Leu Ile Gln Asn Asn Ile Tyr Asn Ile Thr Lys
                165                 170                 175

Glu Gly Ile Ser Arg Leu Ile Asn Leu Lys Asn Leu Tyr Leu Ala Trp
            180                 185                 190

Asn Cys Tyr Phe Asn Lys Val Cys Glu Lys Thr Asn Ile Glu Asp Gly
        195                 200                 205
```

-continued

```
Val Phe Glu Thr Leu Thr Asn Leu Glu Leu Leu Ser Leu Ser Phe Asn
    210                 215                 220

Ser Leu Ser His Val Pro Pro Lys Leu Pro Ser Ser Leu Arg Lys Leu
225                 230                 235                 240

Phe Leu Ser Asn Thr Gln Ile Lys Tyr Ile Ser Glu Glu Asp Phe Lys
                245                 250                 255

Gly Leu Ile Asn Leu Thr Leu Leu Asp Leu Ser Gly Asn Cys Pro Arg
            260                 265                 270

Cys Phe Asn Ala Pro Phe Pro Cys Val Pro Cys Asp Gly Gly Ala Ser
        275                 280                 285

Ile Asn Ile Asp Arg Phe Ala Phe Gln Asn Leu Thr Gln Leu Arg Tyr
    290                 295                 300

Leu Asn Leu Ser Ser Thr Ser Leu Arg Lys Ile Asn Ala Ala Trp Phe
305                 310                 315                 320

Lys Asn Met Pro His Leu Lys Val Leu Asp Leu Glu Phe Asn Tyr Leu
                325                 330                 335

Val Gly Glu Ile Ala Ser Gly Ala Phe Leu Thr Met Leu Pro Arg Leu
            340                 345                 350

Glu Ile Leu Asp Leu Ser Phe Asn Tyr Ile Lys Gly Ser Tyr Pro Gln
        355                 360                 365

His Ile Asn Ile Ser Arg Asn Phe Ser Lys Leu Leu Ser Leu Arg Ala
    370                 375                 380

Leu His Leu Arg Gly Tyr Val Phe Gln Glu Leu Arg Glu Asp Asp Phe
385                 390                 395                 400

Gln Pro Leu Met Gln Leu Pro Asn Leu Ser Thr Ile Asn Leu Gly Ile
                405                 410                 415

Asn Phe Ile Lys Gln Ile Asp Phe Lys Leu Phe Gln Asn Phe Ser Asn
            420                 425                 430

Leu Glu Ile Ile Tyr Leu Ser Glu Asn Arg Ile Ser Pro Leu Val Lys
        435                 440                 445

Asp Thr Arg Gln Ser Tyr Ala Asn Ser Ser Ser Phe Gln Arg His Ile
    450                 455                 460

Arg Lys Arg Arg Ser Thr Asp Phe Glu Phe Asp Pro His Ser Asn Phe
465                 470                 475                 480

Tyr His Phe Thr Arg Pro Leu Ile Lys Pro Gln Cys Ala Ala Tyr Gly
                485                 490                 495

Lys Ala Leu Asp Leu Ser Leu Asn Ser Ile Phe Phe Ile Gly Pro Asn
            500                 505                 510

Gln Phe Glu Asn Leu Pro Asp Ile Ala Cys Leu Asn Leu Ser Ala Asn
        515                 520                 525

Ser Asn Ala Gln Val Leu Ser Gly Thr Glu Phe Ser Ala Ile Pro His
    530                 535                 540

Val Lys Tyr Leu Asp Leu Thr Asn Asn Arg Leu Asp Phe Asp Asn Ala
545                 550                 555                 560

Ser Ala Leu Thr Glu Leu Ser Asp Leu Glu Val Leu Asp Leu Ser Tyr
                565                 570                 575

Asn Ser His Tyr Phe Arg Ile Ala Gly Val Thr His His Leu Glu Phe
            580                 585                 590

Ile Gln Asn Phe Thr Asn Leu Lys Val Leu Asn Leu Ser His Asn Asn
        595                 600                 605

Ile Tyr Thr Leu Thr Asp Lys Tyr Asn Leu Glu Ser Lys Ser Leu Val
    610                 615                 620
```

-continued

```
Glu Leu Val Phe Ser Gly Asn Arg Leu Asp Ile Leu Trp Asn Asp Asp
625                 630                 635                 640

Asp Asn Arg Tyr Ile Ser Ile Phe Lys Gly Leu Lys Asn Leu Thr Arg
                645                 650                 655

Leu Asp Leu Ser Leu Asn Arg Leu Lys His Ile Pro Asn Glu Ala Phe
            660                 665                 670

Leu Asn Leu Pro Ala Ser Leu Thr Glu Leu His Ile Asn Asp Asn Met
        675                 680                 685

Leu Lys Phe Phe Asn Trp Thr Leu Leu Gln Gln Phe Pro Arg Leu Glu
    690                 695                 700

Leu Leu Asp Leu Arg Gly Asn Lys Leu Leu Phe Leu Thr Asp Ser Leu
705                 710                 715                 720

Ser Asp Phe Thr Ser Ser Leu Arg Thr Leu Leu Leu Ser His Asn Arg
                725                 730                 735

Ile Ser His Leu Pro Ser Gly Phe Leu Ser Glu Val Ser Ser Leu Lys
            740                 745                 750

His Leu Asp Leu Ser Ser Asn Leu Leu Lys Thr Ile Asn Lys Ser Ala
        755                 760                 765

Leu Glu Thr Lys Thr Thr Thr Lys Leu Ser Met Leu Glu Leu His Gly
    770                 775                 780

Asn Pro Phe Glu Cys Thr Cys Asp Ile Gly Asp Phe Arg Arg Trp Met
785                 790                 795                 800

Asp Glu His Leu Asn Val Lys Ile Pro Arg Leu Val Asp Val Ile Cys
                805                 810                 815

Ala Ser Pro Gly Asp Gln Arg Gly Lys Ser Ile Val Ser Leu Glu Leu
            820                 825                 830

Thr Thr Cys Val Ser Asp Val Thr Ala Val Ile Leu Phe Phe Phe Thr
        835                 840                 845

Phe Phe Ile Thr Thr Met Val Met Leu Ala Ala Leu Ala His His Leu
    850                 855                 860

Phe Tyr Trp Asp Val Trp Phe Ile Tyr Asn Val Cys Leu Ala Lys Val
865                 870                 875                 880

Lys Gly Tyr Arg Ser Leu Ser Thr Ser Gln Thr Phe Tyr Asp Ala Tyr
                885                 890                 895

Ile Ser Tyr Asp Thr Lys Asp Ala Ser Val Thr Asp Trp Val Ile Asn
            900                 905                 910

Glu Leu Arg Tyr His Leu Glu Glu Ser Arg Asp Lys Asn Val Leu Leu
        915                 920                 925

Cys Leu Glu Glu Arg Asp Trp Asp Pro Gly Leu Ala Ile Ile Asp Asn
    930                 935                 940

Leu Met Gln Ser Ile Asn Gln Ser Lys Lys Thr Val Phe Val Leu Thr
945                 950                 955                 960

Lys Lys Tyr Ala Lys Ser Trp Asn Phe Lys Thr Ala Phe Tyr Leu Ala
                965                 970                 975

Leu Gln Arg Leu Met Asp Glu Asn Met Asp Val Ile Ile Phe Ile Leu
            980                 985                 990

Leu Glu Pro Val Leu Gln His Ser  Gln Tyr Leu Arg Leu  Arg Gln Arg
        995                 1000                1005

Ile Cys  Lys Ser Ser Ile Leu  Gln Trp Pro Asp Asn  Pro Lys Ala
    1010                1015                1020

Glu Gly  Leu Phe Trp Gln Thr  Leu Arg Asn Val Val  Leu Thr Glu
    1025                1030                1035

Asn Asp  Ser Arg Tyr Asn Asn  Met Tyr Val Asp Ser  Ile Lys Gln
```

-continued

```
    1040                1045                1050

Tyr


<210> SEQ ID NO 7
<211> LENGTH: 3468
<212> TYPE: DNA
<213> ORGANISM: Homo sapiens
<220> FEATURE:
<221> NAME/KEY: CDS
<222> LOCATION: (152)..(3331)

<400> SEQUENCE: 7

ctcctgcata gagggtacca ttctgcgctg ctgcaagtta cggaatgaaa aattagaaca      60

acagaaacat ggttctcttg acacttcagt gttagggaac atcagcaaga cccatcccag     120

gagaccttga aggaagcctt tgaaagggag a atg aag gag tca tct ttg caa       172
                                   Met Lys Glu Ser Ser Leu Gln
                                   1               5

aat agc tcc tgc agc ctg gga aag gag act aaa aag gaa aac atg ttc      220
Asn Ser Ser Cys Ser Leu Gly Lys Glu Thr Lys Lys Glu Asn Met Phe
        10                  15                  20

ctt cag tcg tca atg ctg acc tgc att ttc ctg cta ata tct ggt tcc      268
Leu Gln Ser Ser Met Leu Thr Cys Ile Phe Leu Leu Ile Ser Gly Ser
    25                  30                  35

tgt gag tta tgc gcc gaa gaa aat ttt tct aga agc tat cct tgt gat      316
Cys Glu Leu Cys Ala Glu Glu Asn Phe Ser Arg Ser Tyr Pro Cys Asp
40                  45                  50                  55

gag aaa aag caa aat gac tca gtt att gca gag tgc agc aat cgt cga      364
Glu Lys Lys Gln Asn Asp Ser Val Ile Ala Glu Cys Ser Asn Arg Arg
                60                  65                  70

cta cag gaa gtt ccc caa acg gtg ggc aaa tat gtg aca gaa cta gac      412
Leu Gln Glu Val Pro Gln Thr Val Gly Lys Tyr Val Thr Glu Leu Asp
            75                  80                  85

ctg tct gat aat ttc atc aca cac ata acg aat gaa tca ttt caa ggg      460
Leu Ser Asp Asn Phe Ile Thr His Ile Thr Asn Glu Ser Phe Gln Gly
        90                  95                  100

ctg caa aat ctc act aaa ata aat cta aac cac aac ccc aat gta cag      508
Leu Gln Asn Leu Thr Lys Ile Asn Leu Asn His Asn Pro Asn Val Gln
    105                 110                 115

cac cag aac gga aat ccc ggt ata caa tca aat ggc ttg aat atc aca      556
His Gln Asn Gly Asn Pro Gly Ile Gln Ser Asn Gly Leu Asn Ile Thr
120                 125                 130                 135

gac ggg gca ttc ctc aac cta aaa aac cta agg gag tta ctg ctt gaa      604
Asp Gly Ala Phe Leu Asn Leu Lys Asn Leu Arg Glu Leu Leu Leu Glu
                140                 145                 150

gac aac cag tta ccc caa ata ccc tct ggt ttg cca gag tct ttg aca      652
Asp Asn Gln Leu Pro Gln Ile Pro Ser Gly Leu Pro Glu Ser Leu Thr
            155                 160                 165

gaa ctt agt cta att caa aac aat ata tac aac ata act aaa gag ggc      700
Glu Leu Ser Leu Ile Gln Asn Asn Ile Tyr Asn Ile Thr Lys Glu Gly
        170                 175                 180

att tca aga ctt ata aac ttg aaa aat ctc tat ttg gcc tgg aac tgc      748
Ile Ser Arg Leu Ile Asn Leu Lys Asn Leu Tyr Leu Ala Trp Asn Cys
    185                 190                 195

tat ttt aac aaa gtt tgc gag aaa act aac ata gaa gat gga gta ttt      796
Tyr Phe Asn Lys Val Cys Glu Lys Thr Asn Ile Glu Asp Gly Val Phe
200                 205                 210                 215

gaa acg ctg aca aat ttg gag ttg cta tca cta tct ttc aat tct ctt      844
Glu Thr Leu Thr Asn Leu Glu Leu Leu Ser Leu Ser Phe Asn Ser Leu
                220                 225                 230
```

-continued

```
tca cac gtg cca ccc aaa ctg cca agc tcc cta cgc aaa ctt ttt ctg      892
Ser His Val Pro Pro Lys Leu Pro Ser Ser Leu Arg Lys Leu Phe Leu
            235                 240                 245

agc aac acc cag atc aaa tac att agt gaa gaa gat ttc aag gga ttg      940
Ser Asn Thr Gln Ile Lys Tyr Ile Ser Glu Glu Asp Phe Lys Gly Leu
        250                 255                 260

ata aat tta aca tta cta gat tta agc ggg aac tgt ccg agg tgc ttc      988
Ile Asn Leu Thr Leu Leu Asp Leu Ser Gly Asn Cys Pro Arg Cys Phe
    265                 270                 275

aat gcc cca ttt cca tgc gtg cct tgt gat ggt ggt gct tca att aat     1036
Asn Ala Pro Phe Pro Cys Val Pro Cys Asp Gly Gly Ala Ser Ile Asn
280                 285                 290                 295

ata gat cgt ttt gct ttt caa aac ttg acc caa ctt cga tac cta aac     1084
Ile Asp Arg Phe Ala Phe Gln Asn Leu Thr Gln Leu Arg Tyr Leu Asn
                300                 305                 310

ctc tct agc act tcc ctc agg aag att aat gct gcc tgg ttt aaa aat     1132
Leu Ser Ser Thr Ser Leu Arg Lys Ile Asn Ala Ala Trp Phe Lys Asn
            315                 320                 325

atg cct cat ctg aag gtg ctg gat ctt gaa ttc aac tat tta gtg gga     1180
Met Pro His Leu Lys Val Leu Asp Leu Glu Phe Asn Tyr Leu Val Gly
        330                 335                 340

gaa ata gcc tct ggg gca ttt tta acg atg ctg ccc cgc tta gaa ata     1228
Glu Ile Ala Ser Gly Ala Phe Leu Thr Met Leu Pro Arg Leu Glu Ile
    345                 350                 355

ctt gac ttg tct ttt aac tat ata aag ggg agt tat cca cag cat att     1276
Leu Asp Leu Ser Phe Asn Tyr Ile Lys Gly Ser Tyr Pro Gln His Ile
360                 365                 370                 375

aat att tcc aga aac ttc tct aaa ctt ttg tct cta cgg gca ttg cat     1324
Asn Ile Ser Arg Asn Phe Ser Lys Leu Leu Ser Leu Arg Ala Leu His
                380                 385                 390

tta aga ggt tat gtg ttc cag gaa ctc aga gaa gat gat ttc cag ccc     1372
Leu Arg Gly Tyr Val Phe Gln Glu Leu Arg Glu Asp Asp Phe Gln Pro
            395                 400                 405

ctg atg cag ctt cca aac tta tcg act atc aac ttg ggt att aat ttt     1420
Leu Met Gln Leu Pro Asn Leu Ser Thr Ile Asn Leu Gly Ile Asn Phe
        410                 415                 420

att aag caa atc gat ttc aaa ctt ttc caa aat ttc tcc aat ctg gaa     1468
Ile Lys Gln Ile Asp Phe Lys Leu Phe Gln Asn Phe Ser Asn Leu Glu
    425                 430                 435

att att tac ttg tca gaa aac aga ata tca ccg ttg gta aaa gat acc     1516
Ile Ile Tyr Leu Ser Glu Asn Arg Ile Ser Pro Leu Val Lys Asp Thr
440                 445                 450                 455

cgg cag agt tat gca aat agt tcc tct ttt caa cgt cat atc cgg aaa     1564
Arg Gln Ser Tyr Ala Asn Ser Ser Ser Phe Gln Arg His Ile Arg Lys
                460                 465                 470

cga cgc tca aca gat ttt gag ttt gac cca cat tcg aac ttt tat cat     1612
Arg Arg Ser Thr Asp Phe Glu Phe Asp Pro His Ser Asn Phe Tyr His
            475                 480                 485

ttc acc cgt cct tta ata aag cca caa tgt gct gct tat gga aaa gcc     1660
Phe Thr Arg Pro Leu Ile Lys Pro Gln Cys Ala Ala Tyr Gly Lys Ala
        490                 495                 500

tta gat tta agc ctc aac agt att ttc ttc att ggg cca aac caa ttt     1708
Leu Asp Leu Ser Leu Asn Ser Ile Phe Phe Ile Gly Pro Asn Gln Phe
    505                 510                 515

gaa aat ctt cct gac att gcc tgt tta aat ctg tct gca aat agc aat     1756
Glu Asn Leu Pro Asp Ile Ala Cys Leu Asn Leu Ser Ala Asn Ser Asn
520                 525                 530                 535

gct caa gtg tta agt gga act gaa ttt tca gcc att cct cat gtc aaa     1804
Ala Gln Val Leu Ser Gly Thr Glu Phe Ser Ala Ile Pro His Val Lys
                540                 545                 550
```

-continued

```
tat ttg gat ttg aca aac aat aga cta gac ttt gat aat gct agt gct     1852
Tyr Leu Asp Leu Thr Asn Asn Arg Leu Asp Phe Asp Asn Ala Ser Ala
            555                 560                 565

ctt act gaa ttg tcc gac ttg gaa gtt cta gat ctc agc tat aat tca     1900
Leu Thr Glu Leu Ser Asp Leu Glu Val Leu Asp Leu Ser Tyr Asn Ser
        570                 575                 580

cac tat ttc aga ata gca ggc gta aca cat cat cta gaa ttt att caa     1948
His Tyr Phe Arg Ile Ala Gly Val Thr His His Leu Glu Phe Ile Gln
    585                 590                 595

aat ttc aca aat cta aaa gtt tta aac ttg agc cac aac aac att tat     1996
Asn Phe Thr Asn Leu Lys Val Leu Asn Leu Ser His Asn Asn Ile Tyr
600                 605                 610                 615

act tta aca gat aag tat aac ctg gaa agc aag tcc ctg gta gaa tta     2044
Thr Leu Thr Asp Lys Tyr Asn Leu Glu Ser Lys Ser Leu Val Glu Leu
                620                 625                 630

gtt ttc agt ggc aat cgc ctt gac att ttg tgg aat gat gat gac aac     2092
Val Phe Ser Gly Asn Arg Leu Asp Ile Leu Trp Asn Asp Asp Asp Asn
            635                 640                 645

agg tat atc tcc att ttc aaa ggt ctc aag aat ctg aca cgt ctg gat     2140
Arg Tyr Ile Ser Ile Phe Lys Gly Leu Lys Asn Leu Thr Arg Leu Asp
        650                 655                 660

tta tcc ctt aat agg ctg aag cac atc cca aat gaa gca ttc ctt aat     2188
Leu Ser Leu Asn Arg Leu Lys His Ile Pro Asn Glu Ala Phe Leu Asn
    665                 670                 675

ttg cca gcg agt ctc act gaa cta cat ata aat gat aat atg tta aag     2236
Leu Pro Ala Ser Leu Thr Glu Leu His Ile Asn Asp Asn Met Leu Lys
680                 685                 690                 695

ttt ttt aac tgg aca tta ctc cag cag ttt cct cgt ctc gag ttg ctt     2284
Phe Phe Asn Trp Thr Leu Leu Gln Gln Phe Pro Arg Leu Glu Leu Leu
                700                 705                 710

gac tta cgt gga aac aaa cta ctc ttt tta act gat agc cta tct gac     2332
Asp Leu Arg Gly Asn Lys Leu Leu Phe Leu Thr Asp Ser Leu Ser Asp
            715                 720                 725

ttt aca tct tcc ctt cgg aca ctg ctg ctg agt cat aac agg att tcc     2380
Phe Thr Ser Ser Leu Arg Thr Leu Leu Leu Ser His Asn Arg Ile Ser
        730                 735                 740

cac cta ccc tct ggc ttt ctt tct gaa gtc agt agt ctg aag cac ctc     2428
His Leu Pro Ser Gly Phe Leu Ser Glu Val Ser Ser Leu Lys His Leu
    745                 750                 755

gat tta agt tcc aat ctg cta aaa aca atc aac aaa tcc gca ctt gaa     2476
Asp Leu Ser Ser Asn Leu Leu Lys Thr Ile Asn Lys Ser Ala Leu Glu
760                 765                 770                 775

act aag acc acc acc aaa tta tct atg ttg gaa cta cac gga aac ccc     2524
Thr Lys Thr Thr Thr Lys Leu Ser Met Leu Glu Leu His Gly Asn Pro
                780                 785                 790

ttt gaa tgc acc tgt gac att gga gat ttc cga aga tgg atg gat gaa     2572
Phe Glu Cys Thr Cys Asp Ile Gly Asp Phe Arg Arg Trp Met Asp Glu
            795                 800                 805

cat ctg aat gtc aaa att ccc aga ctg gta gat gtc att tgt gcc agt     2620
His Leu Asn Val Lys Ile Pro Arg Leu Val Asp Val Ile Cys Ala Ser
        810                 815                 820

cct ggg gat caa aga ggg aag agt att gtg agt ctg gag cta aca act     2668
Pro Gly Asp Gln Arg Gly Lys Ser Ile Val Ser Leu Glu Leu Thr Thr
    825                 830                 835

tgt gtt tca gat gtc act gca gtg ata tta ttt ttc ttc acg ttc ttt     2716
Cys Val Ser Asp Val Thr Ala Val Ile Leu Phe Phe Phe Thr Phe Phe
840                 845                 850                 855

atc acc acc atg gtt atg ttg gct gcc ctg gct cac cat ttg ttt tac     2764
Ile Thr Thr Met Val Met Leu Ala Ala Leu Ala His His Leu Phe Tyr
```

-continued

```
            860                 865                 870

tgg gat gtt tgg ttt ata tat aat gtg tgt tta gct aag gta aaa ggc     2812
Trp Asp Val Trp Phe Ile Tyr Asn Val Cys Leu Ala Lys Val Lys Gly
            875                 880                 885

tac agg tct ctt tcc aca tcc caa act ttc tat gat gct tac att tct     2860
Tyr Arg Ser Leu Ser Thr Ser Gln Thr Phe Tyr Asp Ala Tyr Ile Ser
        890                 895                 900

tat gac acc aaa gat gcc tct gtt act gac tgg gtg ata aat gag ctg     2908
Tyr Asp Thr Lys Asp Ala Ser Val Thr Asp Trp Val Ile Asn Glu Leu
    905                 910                 915

cgc tac cac ctt gaa gag agc cga gac aaa aac gtt ctc ctt tgt cta     2956
Arg Tyr His Leu Glu Glu Ser Arg Asp Lys Asn Val Leu Leu Cys Leu
920                 925                 930                 935

gag gag agg gat tgg gat ccg gga ttg gcc atc atc gac aac ctc atg     3004
Glu Glu Arg Asp Trp Asp Pro Gly Leu Ala Ile Ile Asp Asn Leu Met
            940                 945                 950

cag agc atc aac caa agc aag aaa aca gta ttt gtt tta acc aaa aaa     3052
Gln Ser Ile Asn Gln Ser Lys Lys Thr Val Phe Val Leu Thr Lys Lys
            955                 960                 965

tat gca aaa agc tgg aac ttt aaa aca gct ttt tac ttg gct ttg cag     3100
Tyr Ala Lys Ser Trp Asn Phe Lys Thr Ala Phe Tyr Leu Ala Leu Gln
        970                 975                 980

agg cta atg gat gag aac atg gat gtg att ata ttt atc ctg ctg gag     3148
Arg Leu Met Asp Glu Asn Met Asp Val Ile Ile Phe Ile Leu Leu Glu
    985                 990                 995

cca  gtg tta cag cat tct  cag tat ttg agg cta  cgg cag cgg atc      3193
Pro  Val Leu Gln His Ser  Gln Tyr Leu Arg Leu  Arg Gln Arg Ile
1000                 1005                 1010

tgt  aag agc tcc atc ctc  cag tgg cct gac aac  ccg aag gca gaa      3238
Cys  Lys Ser Ser Ile Leu  Gln Trp Pro Asp Asn  Pro Lys Ala Glu
1015                 1020                 1025

ggc  ttg ttt tgg caa act  ctg aga aat gtg gtc  ttg act gaa aat      3283
Gly  Leu Phe Trp Gln Thr  Leu Arg Asn Val Val  Leu Thr Glu Asn
1030                 1035                 1040

gat  tca cgg tat aac aat  atg tat gtc gat tcc  att aag caa tac      3328
Asp  Ser Arg Tyr Asn Asn  Met Tyr Val Asp Ser  Ile Lys Gln Tyr
1045                 1050                 1055

taa ctgacgttaa gtcatgattt cgcgccataa taaagatgca aaggaatgac         3381

atttctgtat tagttatcta ttgctatgta acaaattatc ccaaaactta gtggtttaaa   3441

acaacacatt tgctggccca cagtttt                                       3468


<210> SEQ ID NO 8
<211> LENGTH: 1059
<212> TYPE: PRT
<213> ORGANISM: Homo sapiens

<400> SEQUENCE: 8

Met Lys Glu Ser Ser Leu Gln Asn Ser Ser Cys Ser Leu Gly Lys Glu
1               5                   10                  15

Thr Lys Lys Glu Asn Met Phe Leu Gln Ser Ser Met Leu Thr Cys Ile
            20                  25                  30

Phe Leu Leu Ile Ser Gly Ser Cys Glu Leu Cys Ala Glu Glu Asn Phe
        35                  40                  45

Ser Arg Ser Tyr Pro Cys Asp Glu Lys Lys Gln Asn Asp Ser Val Ile
    50                  55                  60

Ala Glu Cys Ser Asn Arg Arg Leu Gln Glu Val Pro Gln Thr Val Gly
65                  70                  75                  80
```

-continued

```
Lys Tyr Val Thr Glu Leu Asp Leu Ser Asp Asn Phe Ile Thr His Ile
                85                  90                  95

Thr Asn Glu Ser Phe Gln Gly Leu Gln Asn Leu Thr Lys Ile Asn Leu
            100                 105                 110

Asn His Asn Pro Asn Val Gln His Gln Asn Gly Asn Pro Gly Ile Gln
        115                 120                 125

Ser Asn Gly Leu Asn Ile Thr Asp Gly Ala Phe Leu Asn Leu Lys Asn
    130                 135                 140

Leu Arg Glu Leu Leu Leu Glu Asp Asn Gln Leu Pro Gln Ile Pro Ser
145                 150                 155                 160

Gly Leu Pro Glu Ser Leu Thr Glu Leu Ser Leu Ile Gln Asn Asn Ile
                165                 170                 175

Tyr Asn Ile Thr Lys Glu Gly Ile Ser Arg Leu Ile Asn Leu Lys Asn
            180                 185                 190

Leu Tyr Leu Ala Trp Asn Cys Tyr Phe Asn Lys Val Cys Glu Lys Thr
        195                 200                 205

Asn Ile Glu Asp Gly Val Phe Glu Thr Leu Thr Asn Leu Glu Leu Leu
    210                 215                 220

Ser Leu Ser Phe Asn Ser Leu Ser His Val Pro Pro Lys Leu Pro Ser
225                 230                 235                 240

Ser Leu Arg Lys Leu Phe Leu Ser Asn Thr Gln Ile Lys Tyr Ile Ser
                245                 250                 255

Glu Glu Asp Phe Lys Gly Leu Ile Asn Leu Thr Leu Leu Asp Leu Ser
            260                 265                 270

Gly Asn Cys Pro Arg Cys Phe Asn Ala Pro Phe Pro Cys Val Pro Cys
        275                 280                 285

Asp Gly Gly Ala Ser Ile Asn Ile Asp Arg Phe Ala Phe Gln Asn Leu
    290                 295                 300

Thr Gln Leu Arg Tyr Leu Asn Leu Ser Ser Thr Ser Leu Arg Lys Ile
305                 310                 315                 320

Asn Ala Ala Trp Phe Lys Asn Met Pro His Leu Lys Val Leu Asp Leu
                325                 330                 335

Glu Phe Asn Tyr Leu Val Gly Glu Ile Ala Ser Gly Ala Phe Leu Thr
            340                 345                 350

Met Leu Pro Arg Leu Glu Ile Leu Asp Leu Ser Phe Asn Tyr Ile Lys
        355                 360                 365

Gly Ser Tyr Pro Gln His Ile Asn Ile Ser Arg Asn Phe Ser Lys Leu
    370                 375                 380

Leu Ser Leu Arg Ala Leu His Leu Arg Gly Tyr Val Phe Gln Glu Leu
385                 390                 395                 400

Arg Glu Asp Asp Phe Gln Pro Leu Met Gln Leu Pro Asn Leu Ser Thr
                405                 410                 415

Ile Asn Leu Gly Ile Asn Phe Ile Lys Gln Ile Asp Phe Lys Leu Phe
            420                 425                 430

Gln Asn Phe Ser Asn Leu Glu Ile Ile Tyr Leu Ser Glu Asn Arg Ile
        435                 440                 445

Ser Pro Leu Val Lys Asp Thr Arg Gln Ser Tyr Ala Asn Ser Ser Ser
    450                 455                 460

Phe Gln Arg His Ile Arg Lys Arg Arg Ser Thr Asp Phe Glu Phe Asp
465                 470                 475                 480

Pro His Ser Asn Phe Tyr His Phe Thr Arg Pro Leu Ile Lys Pro Gln
                485                 490                 495

Cys Ala Ala Tyr Gly Lys Ala Leu Asp Leu Ser Leu Asn Ser Ile Phe
```

-continued

```
            500                 505                 510

Phe Ile Gly Pro Asn Gln Phe Glu Asn Leu Pro Asp Ile Ala Cys Leu
        515                 520                 525

Asn Leu Ser Ala Asn Ser Asn Ala Gln Val Leu Ser Gly Thr Glu Phe
    530                 535                 540

Ser Ala Ile Pro His Val Lys Tyr Leu Asp Leu Thr Asn Asn Arg Leu
545                 550                 555                 560

Asp Phe Asp Asn Ala Ser Ala Leu Thr Glu Leu Ser Asp Leu Glu Val
                565                 570                 575

Leu Asp Leu Ser Tyr Asn Ser His Tyr Phe Arg Ile Ala Gly Val Thr
            580                 585                 590

His His Leu Glu Phe Ile Gln Asn Phe Thr Asn Leu Lys Val Leu Asn
        595                 600                 605

Leu Ser His Asn Asn Ile Tyr Thr Leu Thr Asp Lys Tyr Asn Leu Glu
    610                 615                 620

Ser Lys Ser Leu Val Glu Leu Val Phe Ser Gly Asn Arg Leu Asp Ile
625                 630                 635                 640

Leu Trp Asn Asp Asp Asp Asn Arg Tyr Ile Ser Ile Phe Lys Gly Leu
                645                 650                 655

Lys Asn Leu Thr Arg Leu Asp Leu Ser Leu Asn Arg Leu Lys His Ile
            660                 665                 670

Pro Asn Glu Ala Phe Leu Asn Leu Pro Ala Ser Leu Thr Glu Leu His
        675                 680                 685

Ile Asn Asp Asn Met Leu Lys Phe Phe Asn Trp Thr Leu Leu Gln Gln
    690                 695                 700

Phe Pro Arg Leu Glu Leu Leu Asp Leu Arg Gly Asn Lys Leu Leu Phe
705                 710                 715                 720

Leu Thr Asp Ser Leu Ser Asp Phe Thr Ser Ser Leu Arg Thr Leu Leu
                725                 730                 735

Leu Ser His Asn Arg Ile Ser His Leu Pro Ser Gly Phe Leu Ser Glu
            740                 745                 750

Val Ser Ser Leu Lys His Leu Asp Leu Ser Ser Asn Leu Leu Lys Thr
        755                 760                 765

Ile Asn Lys Ser Ala Leu Glu Thr Lys Thr Thr Thr Lys Leu Ser Met
    770                 775                 780

Leu Glu Leu His Gly Asn Pro Phe Glu Cys Thr Cys Asp Ile Gly Asp
785                 790                 795                 800

Phe Arg Arg Trp Met Asp Glu His Leu Asn Val Lys Ile Pro Arg Leu
                805                 810                 815

Val Asp Val Ile Cys Ala Ser Pro Gly Asp Gln Arg Gly Lys Ser Ile
            820                 825                 830

Val Ser Leu Glu Leu Thr Thr Cys Val Ser Asp Val Thr Ala Val Ile
        835                 840                 845

Leu Phe Phe Phe Thr Phe Phe Ile Thr Thr Met Val Met Leu Ala Ala
    850                 855                 860

Leu Ala His His Leu Phe Tyr Trp Asp Val Trp Phe Ile Tyr Asn Val
865                 870                 875                 880

Cys Leu Ala Lys Val Lys Gly Tyr Arg Ser Leu Ser Thr Ser Gln Thr
                885                 890                 895

Phe Tyr Asp Ala Tyr Ile Ser Tyr Asp Thr Lys Asp Ala Ser Val Thr
            900                 905                 910

Asp Trp Val Ile Asn Glu Leu Arg Tyr His Leu Glu Glu Ser Arg Asp
        915                 920                 925
```

-continued

```
Lys Asn Val Leu Leu Cys Leu Glu Glu Arg Asp Trp Asp Pro Gly Leu
    930                 935                 940

Ala Ile Ile Asp Asn Leu Met Gln Ser Ile Asn Gln Ser Lys Lys Thr
945                 950                 955                 960

Val Phe Val Leu Thr Lys Lys Tyr Ala Lys Ser Trp Asn Phe Lys Thr
                965                 970                 975

Ala Phe Tyr Leu Ala Leu Gln Arg Leu Met Asp Glu Asn Met Asp Val
            980                 985                 990

Ile Ile Phe Ile Leu Leu Glu Pro  Val Leu Gln His Ser  Gln Tyr Leu
        995                 1000                 1005

Arg Leu  Arg Gln Arg Ile Cys  Lys Ser Ser Ile Leu  Gln Trp Pro
    1010                 1015                 1020

Asp Asn  Pro Lys Ala Glu Gly  Leu Phe Trp Gln Thr  Leu Arg Asn
    1025                 1030                 1035

Val Val  Leu Thr Glu Asn Asp  Ser Arg Tyr Asn Asn  Met Tyr Val
    1040                 1045                 1050

Asp Ser  Ile Lys Gln Tyr
    1055
```

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
ctaactagag aacccactgc 20

<210> SEQ ID NO 10
<211> LENGTH: 42
<212> TYPE: DNA
<213> ORGANISM: Artificial
<220> FEATURE:
<223> OTHER INFORMATION: Primer

<400> SEQUENCE: 10
gatgcacatg ttgtttttg atacacagtt gcatctgaaa tc 42

<210> SEQ ID NO 11
<211> LENGTH: 42
<212> TYPE: DNA
<213> ORGANISM: Artificial
<220> FEATURE:
<223> OTHER INFORMATION: Primer

<400> SEQUENCE: 11
gatttcagat gcaactgtgt atcaaaaaac aacatgtgca tc 42

<210> SEQ ID NO 12
<211> LENGTH: 21
<212> TYPE: DNA
<213> ORGANISM: Artificial
<220> FEATURE:
<223> OTHER INFORMATION: Primer

<400> SEQUENCE: 12
cttcacttga atctcctgaa g 21

<210> SEQ ID NO 13
<211> LENGTH: 20

<212> TYPE: DNA
<213> ORGANISM: Artificial
<220> FEATURE:
<223> OTHER INFORMATION: Primer

<400> SEQUENCE: 13
ctaactagag aacccactgc 20

<210> SEQ ID NO 14
<211> LENGTH: 40
<212> TYPE: DNA
<213> ORGANISM: Artificial
<220> FEATURE:
<223> OTHER INFORMATION: Primer

<400> SEQUENCE: 14
gattgtatac cgggatttcc attggggttg tggtttagat 40

<210> SEQ ID NO 15
<211> LENGTH: 40
<212> TYPE: DNA
<213> ORGANISM: Artificial
<220> FEATURE:
<223> OTHER INFORMATION: Primer

<400> SEQUENCE: 15
atctaaacca caaccccaat ggaaatcccg gtatacaatc 40

<210> SEQ ID NO 16
<211> LENGTH: 25
<212> TYPE: DNA
<213> ORGANISM: Artificial
<220> FEATURE:
<223> OTHER INFORMATION: Primer

<400> SEQUENCE: 16
atcttttacc aacggtgata ttctg 25

<210> SEQ ID NO 17
<211> LENGTH: 27
<212> TYPE: DNA
<213> ORGANISM: Artificial
<220> FEATURE:
<223> OTHER INFORMATION: DNA sequence encoding initiation methionine and FLAG epitope

<400> SEQUENCE: 17
atggattaca aagacgatga cgataaa 27

<210> SEQ ID NO 18
<211> LENGTH: 9
<212> TYPE: PRT
<213> ORGANISM: Artificial
<220> FEATURE:
<223> OTHER INFORMATION: Initiation methionine and FLAG epitope

<400> SEQUENCE: 18

Met Asp Tyr Lys Asp Asp Asp Asp Lys
1 5

<210> SEQ ID NO 19
<211> LENGTH: 11
<212> TYPE: DNA

-continued

<213> ORGANISM: Artificial
<220> FEATURE:
<223> OTHER INFORMATION: NFKB binding site

<400> SEQUENCE: 19
ggggactttc c 11